United States Patent
Guillemont et al.

(10) Patent No.: US 10,150,761 B2
(45) Date of Patent: Dec. 11, 2018

(54) SUBSTITUTED PYRIDINE-PIPERAZINYL ANALOGUES AS RSV ANTIVIRAL COMPOUNDS

(71) Applicant: Janssen Sciences Ireland UC, County Cork (IE)

(72) Inventors: Jerôme Emile Georges Guillemont, Andé (FR); David Francis Alain Lançois, Louviers (FR); Magali Madeleine Simone Motte, Louviers (FR); Delphine Yvonne Raymonde Lardeau, Louviers (FR); Xavier Marc Bourdrez, Louviers (FR); Wendy Mia Albert Balemans, Kalmthout (BE); Dirk André Emmy Roymans, Turnhout (BE)

(73) Assignee: Janssen Sciences Ireland UC, Little Island, County Cork (IE)

(*) Notice: Subject to any disclaimer, the term of this patent is extended or adjusted under 35 U.S.C. 154(b) by 0 days.

(21) Appl. No.: 15/632,027

(22) Filed: Jun. 23, 2017

(65) Prior Publication Data
US 2017/0291891 A1    Oct. 12, 2017

Related U.S. Application Data

(63) Continuation of application No. 14/908,866, filed as application No. PCT/EP2014/066273 on Jul. 29, 2014, now abandoned.

(30) Foreign Application Priority Data

Jul. 30, 2013   (EP) .................... 13178543

(51) Int. Cl.
| | |
|---|---|
| *C07D 409/14* | (2006.01) |
| *C07D 403/04* | (2006.01) |
| *C07D 403/14* | (2006.01) |
| *C07D 241/20* | (2006.01) |
| *C07D 401/12* | (2006.01) |
| *C07D 401/14* | (2006.01) |
| *C07D 405/14* | (2006.01) |
| *C07D 417/14* | (2006.01) |
| *C07D 213/74* | (2006.01) |

(52) U.S. Cl.
CPC ......... *C07D 409/14* (2013.01); *C07D 213/74* (2013.01); *C07D 241/20* (2013.01); *C07D 401/12* (2013.01); *C07D 401/14* (2013.01); *C07D 403/04* (2013.01); *C07D 403/14* (2013.01); *C07D 405/14* (2013.01); *C07D 417/14* (2013.01)

(58) Field of Classification Search
CPC ... C07D 409/14; C07D 213/74; C07D 241/20
See application file for complete search history.

(56) References Cited

U.S. PATENT DOCUMENTS

| | | | |
|---|---|---|---|
| 5,001,125 A | 3/1991 | Stokbroekx et al. | |
| 2008/0194574 A1* | 8/2008 | Eikhoff | C07D 241/20 514/252.11 |
| 2013/0005710 A1 | 1/2013 | Tsukamoto et al. | |
| 2013/0325429 A1 | 12/2013 | Kao et al. | |

FOREIGN PATENT DOCUMENTS

| | | |
|---|---|---|
| CN | 102596946 | 7/2012 |
| EP | 2149373 A1 | 2/2010 |
| WO | 2005058876 A1 | 6/2005 |
| WO | 2006026135 A2 | 3/2006 |
| WO | 200808453 A1 | 1/2008 |
| WO | 2008099210 A2 | 8/2008 |
| WO | 2011015037 A1 | 2/2011 |
| WO | 2011062194 A1 | 5/2011 |
| WO | 2011110852 A1 | 9/2011 |
| WO | 2011143129 A1 | 11/2011 |
| WO | 2011158039 A1 | 12/2011 |
| WO | 2012124696 A1 | 9/2012 |

OTHER PUBLICATIONS

Online Registry VIA STN Apr. 10, 2005, RN 864434-71-9.
Online Registry VIA STN Sep. 9, 2011, RN 1330257-94-7.
Online Registry VIA STN Sep. 9, 2011, RN 1330258-01-9.
Database Registry Chemical Abstracts Service, Columbus, Ohio, Accession No. RN 1452828-98-6, Sep. 20, 2013, XP002732894.
Database Registry Chemical Abstracts Service, Columbus, Ohio, Accession No. RN 1330258-01-9, Nov. 9, 2011, XP002732895.
Database Registry Chemical Abstracts Service, Columbus, Ohio, Accession No. RN 1330257-94-7, Nov. 9, 2011, XP002732896.
Database Registry Chemical Abstracts Service, Columbus, Ohio, Accession No. RN 864434-71-9, Oct. 4, 2005, XP002732897.
Foks, et al, "Studies on Pyrazine Derivatives, XLIV: synthesis and Turbercolostatic Activity of 4-Substituted 3,4,5 6-Tetrahydro-2H-[1,2']-Bis-Pyrazine Derivatives", Phosphorus, Sulfur, and Silicon, vol. 180 (11): pp. 2543-2548 (Jan. 1, 2005).

(Continued)

*Primary Examiner* — Pancham Bakshi

(57) ABSTRACT

The invention concerns novel substituted pyridine-piperazinyl analogs of formula (I) having antiviral activity, in particular, having an inhibitory activity on the replication of the respiratory syncytial virus (RSV). The invention further concerns the preparation of such novel compounds, compositions comprising these compounds, and the compounds for use in the treatment of respiratory syncytial virus infection.

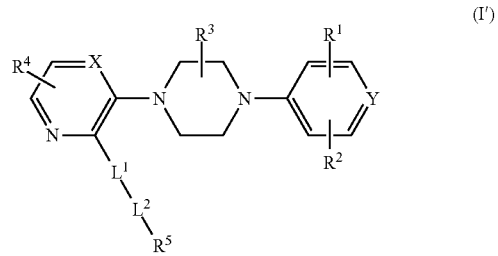

(I')

10 Claims, No Drawings

(56) References Cited

OTHER PUBLICATIONS

Hallack, et al., "Glycosaminoglycan Sulfation Requirements for Respiratory Syncytial Virus Infection", Journal of Virology, vol. 74(22):pp. 10508-10513 (Nov. 2000).
Olszewska, et al, "Emerging drugs for respiratory syncytial virus infection", Expert Opinion, vol. 14 (2) :pp. 207-217 (Jun. 1, 2009).
Wyde, et al., "CL387626 exhibits marked and unusual antiviral activity against respiratory syncytial virus in tissue culture and in cotton rats", Antiviral Research, vol. 38: pp. 31-42 (1998).
International Search Report and Written Opinion dated Dec. 12, 2014, for International Application No. PCT/EP2014/066273.
European Search Report dated Sep. 30, 2013, for European Application No. EP13178543.8.

* cited by examiner

SUBSTITUTED PYRIDINE-PIPERAZINYL ANALOGUES AS RSV ANTIVIRAL COMPOUNDS

CROSS-REFERENCE TO RELATED APPLICATIONS

This application is a continuation of U.S. patent application Ser. No. 14/908,866 filed on Jan. 29, 2016, which is a national stage filing under USC 371 of international application PCT/EP2014/066273 filed on Jul. 29, 2014, which claims priority to European Patent Application No. 13178543.8 filed Jul. 30, 2013 the complete disclosures of which are hereby incorporated herein by reference for all purposes.

FIELD OF THE INVENTION

The invention concerns novel substituted pyridine-piperazinyl analogues having antiviral activity, in particular, having an inhibitory activity on the replication of the respiratory syncytial virus (RSV). The invention further concerns the preparation of such novel compounds, compositions comprising these compounds, and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue that provides an aerosol treatment for serious RSV infection in hospitalized children. The aerosol route of administration, the toxicity (risk of teratogenicity), the cost and the highly variable efficacy limit its use. The other two drugs, RespiGam® (RSV-IG) and Synagis® (palivizumab), polyclonal and monoclonal antibody immunostimulants, are intended to be used in a preventive way. Both are very expensive, and require parenteral administration.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication. It would be particularly preferred to provide drugs against RSV replication that could be administered perorally.

WO-2006/026135 discloses substituted biaryl piperazinyl-pyridine analogues for use in the treatment of conditions related to capsaicin receptor activation. WO-2008/008453 discloses heterocyclic substituted piperazine compounds with CXCR3 antagonistic activity. WO-2008/099210 discloses heteroarylpiperazine derivatives for treatment of Alzheimer's disease and related conditions. WO-2011/143129 discloses nitrogen-heterocyclic compounds as phosphodiesterase 10 inhibitors.

EP-2,149,373 discloses substituted piperazinyl compounds as $5HT_7$ receptor ligands. Foks H. et al. in *Phosphorus, Sulfur, and Silicon*, vol. 180, pp. 2543-2548 (2005) disclose a number of substituted piperazinyl compounds having tuberculostatic activity. WO-2011/015037 discloses compounds having antiviral activity by inhibition of the nucleoprotein of the virus, in particular influenza virus, whereby in one embodiment these compounds are heterocyclic amides containing piperazine and isozazole rings substituted with one or more substituents.

It is desired to provide new drugs that have antiviral activity. Particularly, it would be desired to provide new drugs that have RSV replication inhibitory activity. Further, it would be desired to retrieve compound structures that allow obtaining antiviral biological activities of the order of magnitude in the stronger regions of the prior art (i.e. at the bottom of the above-mentioned range of up to 50 μM), and preferably at a level of about the most active, more preferably of even stronger activity, than the compounds disclosed in the art. A further desire is to find compounds having oral antiviral activity.

SUMMARY OF THE INVENTION

The present invention relates to a compound of formula (I)

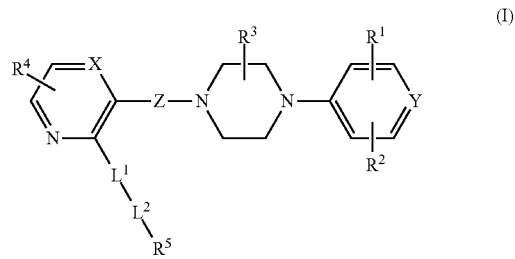

including any stereochemically isomeric form thereof, wherein
X and Y are each independently selected from $CR^6$ or N, wherein $R^6$ is hydrogen, halo, hydroxy, $C_{1-4}$alkyl, $C_{1-4}$alkyloxy, cyano, polyhalo$C_{1-4}$alkyl, polyhalo$C_{1-4}$alkyloxy, nitro, amino, mono- or di($C_{1-4}$alkyl)amino, or $C_{1-4}$alkylcarbonyl;
Z is a direct bond;
$R^1$ and $R^2$ are each independently selected from hydrogen, halo, hydroxy, $C_{1-4}$alkyl, $C_{1-4}$alkyloxy, polyhalo$C_{1-4}$alkyl, polyhalo$C_{1-4}$alkyloxy, cyano, nitro, or $C_{1-4}$alkylcarbonyl:
$R^3$ is hydrogen or $C_{1-6}$alkyl;
$R^4$ is hydrogen, halo, hydroxy, $C_{1-4}$alkyl, $C_{1-4}$alkyloxy, polyhalo$C_{1-4}$alkyl, polyhalo-$C_{1-4}$alkyloxy, cyano, nitro, or $C_{1-4}$alkylcarbonyl;

L¹ is a direct bond; oxygen; $C_{1-4}$alkanediyl; or $C_{1-4}$alkanediyl substituted with one or two substituents each independently selected from hydroxy, phenyl, or phenyl substituted with $C_{1-4}$alkyloxy:

L² is a direct bond, phenyl, piperazine, or piperazine substituted with hydroxy; and R⁵ is $C_{1-4}$alkyl, $C_{3-6}$cycloalkyl, heteroalkyl, aryl or heteroaryl;

wherein heteroalkyl is piperidinyl;
  aryl is phenyl, or naphthalenyl; wherein each aryl is optionally substituted with one or two substituents each independently selected from halo, hydroxy, $C_{1-4}$alkyl, $C_{1-4}$alkyloxy, $C_{1-4}$alkylthio, polyhalo$C_{1-4}$alkyl, polyhalo-$C_{1-4}$alkyloxy, cyano, nitro, amino, mono- or di($C_{1-4}$alkyl)-amino, $C_{1-4}$alkylcarbonyl, or $C_{1-4}$alkyl($SO_2$)—NH—;
  heteroaryl is furanyl, thiophenyl, pyrazolyl, pyridinyl, pyridazinyl, pyrimidinyl, pyrazinyl, 2,3-dihydro-benzo[1,4]dioxinyl, benzo[1,3]dioxolyl, 1-benzofuranyl, 2,3-dihydro-1-benzofuranyl, 1-benzothiophenyl, 1-benzopyrazolyl, 1,3-benzothiazolyl, or quinolinyl; wherein each heteroaryl is optionally substituted with one or two substituents each independently selected from $C_{1-4}$alkyl, $C_{1-4}$alkyloxy, hydroxy$C_{1-4}$alkyl, cyano$C_{1-4}$alkyl, or polyhalo$C_{1-4}$alkyl, or $C_{1-4}$alkyloxy$C_{1-4}$alkyl;

or a pharmaceutically acceptable acid addition salt thereof.

As used in the foregoing definitions:
halo is generic to fluoro, chloro, bromo and iodo;
$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like;
$C_{3-6}$cycloalkyl is generic to cyclopropyl, cyclobutyl, cyclopentyl, and cyclohexyl;
hydroxy$C_{1-4}$alkyl is defined as a $C_{1-4}$alkyl group substituted with one hydroxy group;
cano$C_{1-4}$alkyl is defined as a $C_{1-4}$alkyl group substituted with one cyano group;
polyhalo$C_{1-4}$alkyl is defined as polyhalosubstituted $C_{1-4}$alkyl, in particular $C_{1-4}$alkyl (as hereinabove defined) substituted with 2 to 6 halogen atoms such as difluoromethyl, trifluoromethyl, trifluoroethyl, and the like.

The term "compounds of the invention" as used herein, is meant to include the compounds of formula (I), and the salts and solvates thereof.

Since all compounds of formula (I) have a substituent Z defined as a direct bond, the compounds of formula (I) can be defined equally well with the following Markush formula (I'):

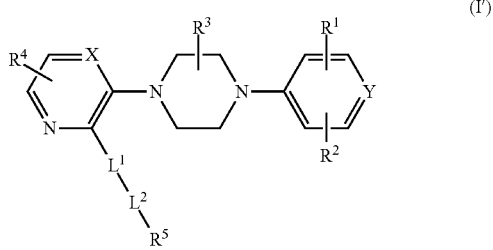

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the terms "compound of formula (I) or (I')" and "intermediates of synthesis of formula (I) or (I')" are meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers. Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration: for example if a compound contains a disubstituted cycloalkyl group, the substituents may be in the cis or trans configuration.

Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

Some of the compounds according to formula (I) or (I') may also exist in their tautomeric form. Such forms in so far as they may exist, although not explicitly indicated in the above formula (I) or (I') are intended to be included within the scope of the present invention.

It follows that a single compound may exist in both stereoisomeric and tautomeric form.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) or (I') may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

Interesting compounds of formula (I') are those compounds of formula (I') wherein one or more of the following restrictions apply:

a) X is N or $CR^6$, wherein $R^6$ is hydrogen;
b) X is $CR^6$, wherein $R^6$ is hydrogen;
c) X is N;
d) Y is N or $CR^6$, wherein $R^6$ is hydrogen:
e) Y is $CR^6$, wherein $R^6$ is hydrogen:
f) Y is N;
g) $R^1$ and $R^2$ are each independently selected from hydrogen, halo, or $C_{1-4}$alkyloxy;
h) $R^3$ is hydrogen or $C_{1-6}$alkyl;
i) $R^3$ is hydrogen;
j) $R^3$ is $C_{1-4}$alkyl;
k) $R^4$ is hydrogen:
l) $L^1$ is a direct bond and $L^2$ is a direct bond:
m) $L^1$ is a direct bond and $L^2$ is phenyl:
n) $L^1$ is oxygen and $L^2$ is a direct bond:
o) $L^1$ is $C_{1-4}$alkanediyl or $C_{1-4}$alkanediyl substituted with hydroxy, and $L^2$ is a direct bond:
p) $R^5$ is aryl; and
q) $R^5$ is heteroaryl.

A first group of compounds of formula (I') are those compounds of formula (I') wherein X is N, and Y is N.

A second group of compounds of formula (I') are those compounds of formula (I') wherein X is N, and Y is $CR^6$ wherein $R^6$ is hydrogen.

A third group of compounds of formula (I') are those compounds of formula (I') wherein X is $CR^6$ wherein $R^6$ is hydrogen, and Y is N.

A fourth group of compounds of formula (I') are those compounds of formula (I') wherein X is $CR^6$ wherein $R^6$ is hydrogen, and Y is $CR^6$ wherein $R^6$ is hydrogen.

A fifth group of compounds of formula (I') are those compounds of formula (I') wherein X is $CR^6$ wherein $R^6$ is hydrogen, Y is N, $L^1$ is a direct bond and $L^2$ is a direct bond.

A sixth group of compounds of formula (I') are those compounds of formula (I') wherein X is N, Y is N, $L^1$ is a direct bond and $L^2$ is a direct bond.

An seventh group of compounds of formula (I') are those compounds of formula (I') wherein X is $CR^6$ wherein $R^6$ is hydrogen, Y is N. $L^1$ is a direct bond, $L^2$ is a direct bond and $R^5$ is aryl.

A eighth group of compounds of formula (I') are those compounds of formula (I') wherein X is N, Y is N, $L^1$ is a direct bond. $L^2$ is a direct bond and $R^5$ is aryl.

In an embodiment the present invention relates to compounds of formula (I')

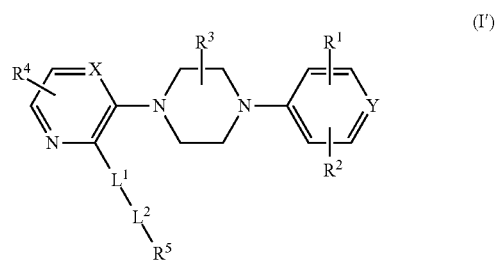

including any stereochemically isomeric form thereof, wherein

X and Y are each independently selected from $CR^6$ or N, wherein $R^6$ is hydrogen;

$R^1$ and $R^2$ are each independently selected from hydrogen, halo, hydroxy, $C_{1-4}$alkyl, or $C_{1-4}$alkyloxy;

$R^3$ is hydrogen or $C_{1-6}$alkyl;

$R^4$ is hydrogen:

$L^1$ is a direct bond; oxygen; $C_{1-4}$alkanediyl; or $C_{1-4}$alkanediyl substituted with one or two substituents each independently selected from hydroxy, phenyl, or phenyl substituted with $C_{1-4}$alkyloxy;

$L^2$ is a direct bond, phenyl, piperazine, or piperazine substituted with hydroxy; and $R^5$ is $C_{1-4}$alkyl, $C_{3-6}$cycloalkyl, heteroalkyl, aryl or heteroaryl;

wherein heteroalkyl is piperidinyl:

aryl is phenyl, or naphthalenyl; wherein each aryl is optionally substituted with one or two substituents each independently selected from halo, hydroxy, $C_{1-4}$alkyl, $C_{1-4}$alkyloxy, $C_{1-4}$alkylthio, polyhalo$C_{1-4}$alkyl, polyhalo$C_{1-4}$alkyloxy, cyano, di($C_{1-4}$alkyl)-amino, $C_{1-4}$alkylcarbonyl, or $C_{1-4}$alkyl(SO$_2$)—NH—;

heteroaryl is furanyl, pyridinyl, 2,3-dihydro-benzo[1,4]dioxinyl, benzo[1,3]dioxolyl, 1-benzofuranyl, 2,3-dihydro-1-benzofuranyl, 1-benzothiophenyl, 1-benzopyrazolyl, 1,3-benzothiazolyl, or quinolinyl; wherein each heteroaryl is optionally substituted with one or two substituents each independently selected from $C_{1-4}$alkyl, $C_{1-4}$alkyloxy, hydroxy$C_{1-4}$alkyl, cyano$C_{1-4}$alkyl, or polyhalo$C_{1-4}$alkyl, or $C_{1-4}$alkyloxy$C_{1-4}$alkyl;

or a pharmaceutically acceptable acid addition salt thereof.

In general compounds of formula (I') can be prepared by reacting an intermediate of formula (II) with an allylboronate intermediate of formula (II), wherein R is an alkyl or cycloalkylgroup, in at least one reaction-inert solvent and optionally in the presence of at least one transition metal coupling reagent and/or at least one suitable ligand, the said process further optionally comprising converting a compound of formula (I) into an addition salt thereof. Suitable metal coupling reagents and/or suitable ligands for this reaction are, e.g. palladium compounds such as palladium tetra(triphenylphosphine), tris(dibenzylidene-acetone dipalladium, 2,2'-bis(diphenylphosphino)-1,1'-binapthyl and the like.

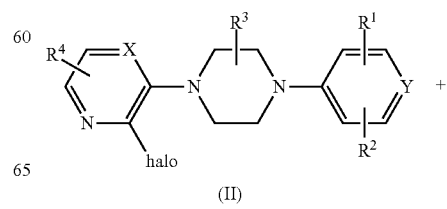

-continued

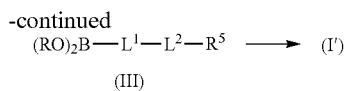

Compounds of formula (I') can also be prepared by reacting an intermediate of formula (IV) under Suzuki coupling conditions with an intermediate of formula (V) wherein one of $L^a$ and Q is selected from bromo, iodo and trifluoromethylsulfonate and the other of $L^a$ and Q is selected from tri($C_{1-4}$alkyl) tin, $B(OH)_2$, alkylboronates and cyclic analogues thereof, in at least one reaction-inert solvent and optionally in the presence of at least one transition metal coupling reagent and/or at least one suitable catalyst such as palladium associated with triphenylphosphine, triphenylarsine and the like.

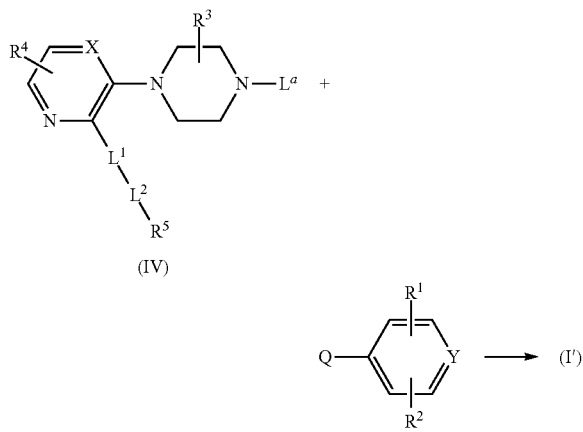

Intermediates of formula (II) can be prepared by reacting an intermediate of formula (VI) with an intermediate of formula (VII), in at least one reaction-inert solvent in the presence of at least one transition metal coupling reagent such as e.g. $Pd_2(dba)_3$ (i.e. tris(dibenzili-deneacetone)dipalladium(0)) and a suitable ligand such as Xantphos (i.e. 4,5-bis(diphenylphosphino)-9,9-dimethylxanthene).

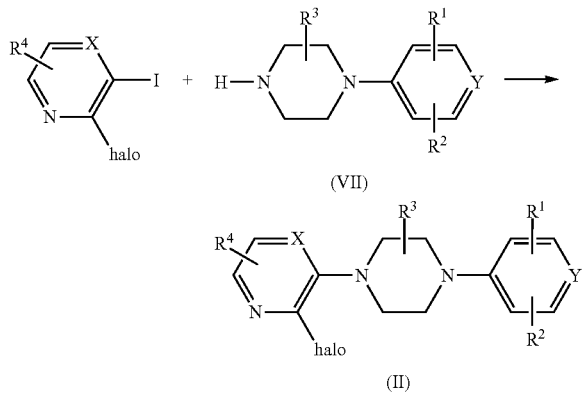

The compounds of formula (I') may further be prepared by converting compounds of formula (I') into each other according to art-known group transformation reactions.

The starting materials and some of the intermediates are known compounds and are commercially available or may be prepared according to conventional reaction procedures generally known in the art.

The compounds of formula (I') as prepared in the hereinabove described processes may be synthesized in the form of racemic mixtures of enantiomers which can be separated from one another following art-known resolution procedures. Those compounds of formula (I') that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I') involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailability, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1', 6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form. e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The invention will hereinafter be illustrated with reference to the following, non-limiting examples.

Experimental Part

Abbreviations

DIPE is defined as diisopropyl ether, DMF is defined as N,N-dimethylformamide, DMSO is defined as dimethyl sulfoxide. EtOAc is defined as ethyl acetate, MeOH is defined as methanol, EtOH is defined as ethanol, THF is defined as tetrahydrofuran, $MgSO_4$ stands for magnesium sulfate, $CH_2Cl_2$ stands for dichloromethane, $CH_3OH$ stands for methanol, DME is defined as dimethoxyethane. NaOH means sodium hydroxide and $NH_4OH$ means ammonium hydroxide.

NMR

For a number of compounds, $^1H$ NMR spectra were recorded on a Bruker DPX-400 spectrometer operating at 400 MHz or on a Bruker DPX-360 operating at 360 MHz using CHLOROFORM-d (deuterated chloroform, $CDCl_3$) or DMSO-$d_6$ (deuterated DMSO, dimethyl-$d_6$ sulfoxide) as solvent. Chemical shifts (δ) are reported in parts per million (ppm) relative to tetramethylsilane (TMS), which was used as internal standard.

A. Synthesis of the Intermediates

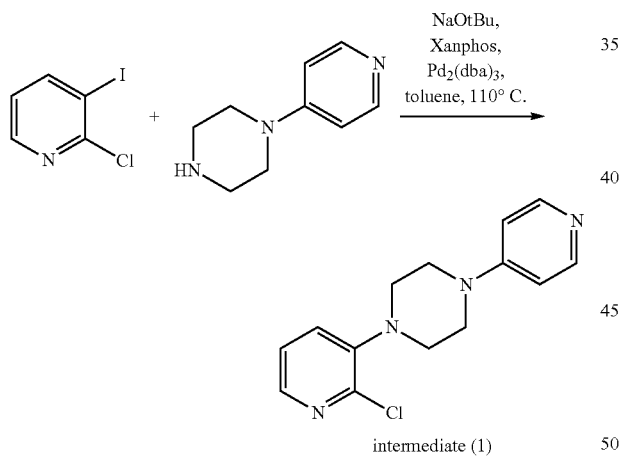

intermediate (1)

EXAMPLE 1

A mixture of 2-chloro-3-iodopyridine (2.0 g, 8.35 mmol), 1-(4-pyridyl)-piperazine (1.64 g, 10.0 mmol), sodium tert-butoxide (1.12 g, 11.7 mmol), 9,9-dimethyl-4,5-bis(diphenyl-phosphino)xanthen (0.24 g, 0.42 mmol) and tris(dibenzylideneacetone)-palladium (0.19 g, 0.209 mmol) in toluene (20 mL) was heated at 110° C. overnight. The mixture was poured out into water and EtOAc. The mixture was filtered through a short pad of Celite® and washed with EtOAc. The organic layer was separated, washed with water and brine, dried over $MgSO_4$ and evaporated till dryness to give 3.0 g of crude product. Purification was carried out by flash chromatography over silica gel (30 μm, Cartridge 80 g, from $CH_2Cl_2$ to $CH_2Cl_2/CH_3OH/NH_4OH$: 93/7/0.1). The pure fractions were collected and evaporated to dryness affording intermediate (1), 1.6 g, 70%.

EXAMPLE 2 a) Preparation of

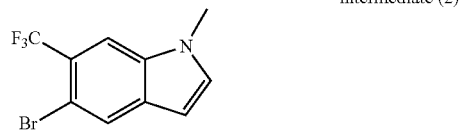

intermediate (2)

Sodium hydride 60% (302.95 mg, 7.574 mmol) was added portionwise to a solution of 5-bromo-6-(trifluoromethyl)-1H-indole (1 g, 3.787 mmol) in DMF (15 mL) at 5° C. under nitrogen atmosphere. The reaction mixture was stirred at 5° C. for 30 minutes then a solution of iodomethane (0.307 mL, 4.923 mmol) was added dropwise at 5° C. The reaction mixture was stirred at 5° C. for 1 hour then at room temperature overnight. The reaction mixture was poured into ice water and EtOAc was added. The organic layer was separated, washed with brine, dried over $MgSO_4$, filtered and the solvent was evaporated until dryness. Purification was carried out by flash chromatography over silica gel (Grace 40 g. heptane 100% to heptane 90%/EtOAc 10%). The pure fractions were collected and evaporated to dryness to afford 0.89 g of intermediate (2).

b) Preparation of

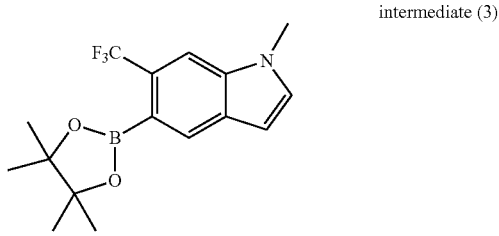

intermediate (3)

A mixture of intermediate (2) (0.75 g, 2.697 mmol), bis(pinacolato)diboron (1.027 g, 4.046 mmol), potassium acetate (0.794 g, 8.091 mmol), and dichloro [1,1'-bis (diphenyl-phosphino) ferrocene] palladium ii dichloromethane adduct (220.806 mg, 0.27 mmol) in dioxane dry (20 mL) was heated and stirred at 80° C. overnight. After cooling to room temperature, the reaction mixture was poured into ice water and EtOAc was added. The mixture was filtered through a pad of Celite® and the Celite® was washed with EtOAc, the filtrate was extracted with EtOAc, washed with brine, dried over $MgSO_4$, filtered and the solvent was evaporated until dryness. Purification of the crude product was carried out by flash chromatography over silica gel (Grace Resolv, 40 g, 35-40 μm), eluent:heptane 100% to heptane 50%/$CH_2Cl_2$ 50%). The pure fractions were collected and evaporated to dryness to afford intermediate (3) (0.180 g, 21%).

EXAMPLE 3 a) Preparation of intermediate (5)

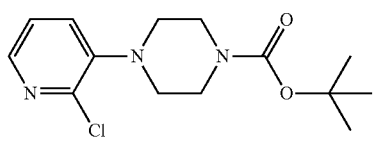

A solution of 2-chloro-3-iodopyridine (5 g, 20.9 mmol), tert-butyl-1-piperazine carboxylate (4.7 g, 25.1 mmol), sodium tert-butoxide (2.81 g, 29.23 mmol), 9,9-dimethyl-4,5-bis-(diphenylphosphino)xanthen (0.6 g, 1.04 mmol) and tris(dibenzy-lideneacetone)palladium (0.48 g, 0.52 mmol) in toluene (50 mL) was heated at 110° C. overnight. The mixture was poured out into water, extracted with EtOAc, the mixture was filtered through a short pad of Celite®, the organic layer was separated, washed with water and brine, dried over MgSO₄ and evaporated till dryness. Purification was carried out by flash chromatography over silica gel (30 µm, cartridge 120 g, heptane/EtOAc: 80/20) The pure fractions were collected and evaporated to dryness to afford 5.1 g (82%) of intermediate (5).

b) Preparation of intermediate (6)

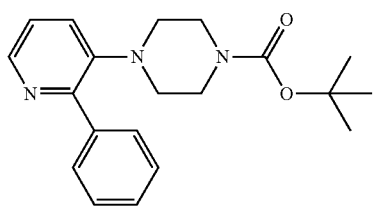

A solution of intermediate (5) (2.4 g, 8.06 mmol) and phenylboronic acid (1.47 g, 12.09 mmol) in potassium carbonate solution 2M (9.7 mL) and DME (24 mL) was purged with nitrogen for 5 minutes then tetrakis (triphenylphosphine)palladium (0.186 g, 0.16 mmol) was added portionwise. The mixture was heated at 100° C. using a singlemode microwave (Biotage initiator 60) with a power output ranging from 0 to 400 W for 40 minutes. Water and EtOAc were added. The organic layer was extracted, dried over MgSO₄, filtered and evaporated to give 0.6 g of crude product. Purification was carried out by chromatography over silicagel (35-40 µm, cartbridge 80 g, CH₂Cl₂/CH₃OH: 99/1). The pure fractions were collected and evaporated to dryness to afford 1.95 g (71%) of intermediate (6).

c) Preparation of intermediate (7)

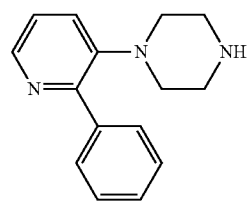

At room temperature, trifluoroacetic acid (2.1 mL; 28.7 mmol) was slowly added to a solution of intermediate (6) (1.95 g, 5.7 mmol) in CH₂Cl₂ (20 mL). The reaction mixture was stirred at room temperature for 24 hours. The solvent was evaporated. Water was added and the aqueous phase was basified with NaOH 3N. The product was extracted with CH₂Cl₂, dried over MgSO₄, filtered and the solvent was evaporated to afford 1.2 g (87%) of intermediate (7).

EXAMPLE 4

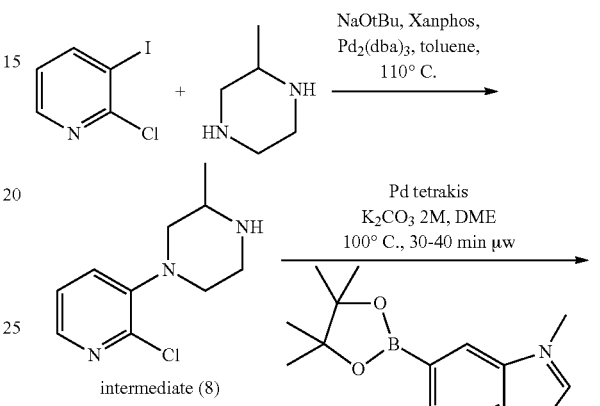

intermediate (9)

a) Preparation of intermediate (8)

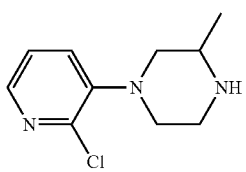

A mixture of 2-chloro-3-iodopyridine (400 mg, 1.67 mmol), 2-methylpiperazine (200 mg, 2.0 mmol), sodium tert-butoxide (224 mg, 2.3 mmol), 9,9-dimethyl-4,5-bis(diphenyl-phosphino)Xanthen (48 mg, 0.08 mmol) and tris (dibenzylideneacetone) palladium (38 mg, 0.04 mmol) in toluene (6 mL) was heated at 110° C. for 18 hours. The mixture was poured out into water, extracted with EtOAc, the mixture was filtered through a short pad of Celite®, the organic layer was separated, washed with water and brine, dried (MgSO₄), evaporated till dryness and the residue was carried out by flash chromatography over silica gel (grace, 40 g, CH₂Cl₂/MeOH/NH₄OH 95/5/0.5) The pure fractions were collected and evaporated to dryness to afford 155 mg (44%) of intermediate (8).

b) Preparation of

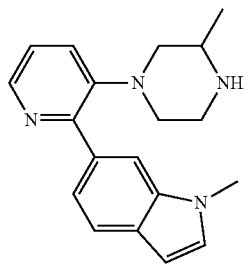

intermediate (9)

A solution of intermediate (8) (150 mg, 0.7 mmol) and 1-methyl-1H-indole-6-boronic acid, pinacol ester (0.219 mg, 0.85 mmol) in potassium carbonate solution (2M, 0.7 mL) and DME (3 mL) was purged with nitrogen for 5 minutes then tetrakis (triphenyl-phosphine)-palladium (82 mg, 0.007 mmol) was added. The mixture was heated at 100° C. using a single mode microwave (Biotage Initiator EXP 60) with a power output ranging from 0 to 400 W for 40 minutes. Water and $CH_2Cl_1$ were added. The organic layer was extracted, dried over $MgSO_4$, filtered and evaporated. The crude product was purified by preparative LC (35-40 µm, 12 g, Grace Resolv), mobile phase: $CH_2Cl_2$/MeOH/$NH_4OH$ 95/5/0.5). The pure fractions were collected and the solvent was evaporated to afford 105 mg (48%) of intermediate (9).

EXAMPLE 5

Preparation of

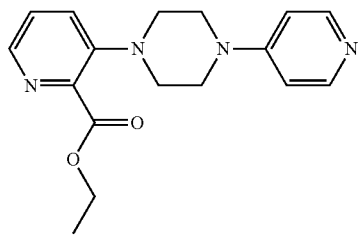

intermediate (10)

Palladium(II) acetate (47% Pd) (8 mg, 0.036 mmol) was added to a solution of intermediate (1) (0.5 g, 1.82 mmol), 1,3-bis(diphenylphosphino)propane (30 mg, 0.073 mmol) and potassium acetate (0.27 g, 2.73 mmol) in EtOH (5 mL) and THF (5 mL) under nitrogen atmosphere then the mixture was stirred under 5 bars of CO at 100° C. for 18 hours in a stainless steel autoclave. The mixture was poured out into water and $CH_2Cl_2$, the organic layer was separated, washed with water, dried over $MgSO_4$ and the solvent evaporated till dryness to give 0.4 g of the crude product. The purification of the crude product was carried out by flash chromatography over silica gel (30 µm, Cartridge 24 g, from $CH_2Cl_2$ to $CH_2Cl_2$/$CH_3OH$/$NH_4OH$: 95/5/0.1). The pure fractions were collected and the solvent was evaporated to dryness to afford 0.23 g (40%) of intermediate (10).

EXAMPLE 6 a) Preparation of

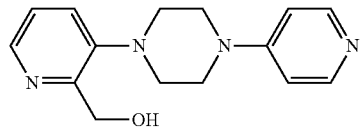

intermediate (11)

The reaction was made under nitrogen atmosphere. Lithium aluminium hydride solution 1M in THF (6.4 mL, 6.4 mmol) was added dropwise to a solution of intermediate (10) (1.0 g, 3.2 mmol) in THF (10 mL) at 5° C., the reaction mixture was stirred at 5° C. for 1 hour. THF/Water (9/1) was added carefully followed by water and $CH_2Cl_2$, the mixture was filtered through a short pad of Celite®, the organic layer was separated and evaporated till dryness to give 0.86 g of a crude product. The purification of the crude product was carried out by flash chromatography over silica gel (30 µm, Cartridge 12 g, from $CH_2Cl_2$ to $CH_2Cl_2CH_3OH$/$NH_4OH$: 95/5/0.5) The pure fractions were collected and evaporated to dryness to afford 0.54 g (62%) of intermediate (11).

b) Preparation of

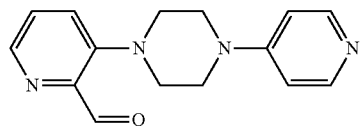

intermediate (12)

A mixture of intermediate (11) (0.34 g, 1.26 mmol) and $MnO_2$ (1.1 g, 12.6 mmol) in $CH_2C_2$ (5 mL) was stirred 18 hours at room temperature. The mixture was filtered through a short pad of Celite® and the filtrate was evaporated till dryness to give 0.26 g (77%) of intermediate (12).

EXAMPLE 7

Preparation of

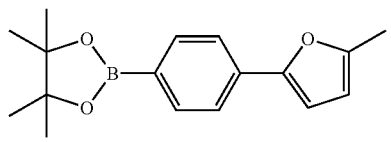

intermediate (13)

The reaction was made under nitrogen atmosphere. A mixture of 2-(4-bromophenyl)-5-methyl-furan mixture (0.54 g, 2.278 mmol), bis(pinacolato)diboron (0.694 g, 2.733 mmol), potassium acetate (0.447 g, 4.555 mmol), and dichloro [1,1'-bis (diphenylphosphino) ferrocene]palladium (II) dichloromethane adduct [CAS number 95464-05-4] (186.46 mg, 0.228 mmol) in dry dioxane (15 mL) was heated at 80° C. during 18 hours in a sealed tube. After cooling to room temperature, the reaction mixture was poured into ice water and EtOAc was added. The organic layer was separated, washed with brine, dried over MgSO₄, filtered and the solvent was evaporated until dryness to give 1.10 g of a crude product. The crude product was purified by preparative LC (stationary phase: irregular SiOH 30 μm 40 g Interchim), mobile phase: 100% heptane to heptane 95/EtOAc 5). The good fractions were collected and the solvent was evaporated to afford 0.41 g (63%) of intermediate (13).

EXAMPLE 8

Preparation of

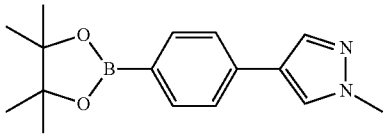

intermediate (14)

A solution of 4-(4-bromophenyl)-1-methyl-1H-pyrazole (0.33 g, 1.18 mmol), bis(pinacolato)diboron (0.36 g, 1.42 mmol) and potassium acetate (0.35 g, 3.55 mmol) in DMF (3.5 mL) and CH₃CN (7 mL) was stirred and degassed with nitrogen for 10 minutes. Ferrocene] palladium (II) dichloromethane adduct (CAS number 95464-05-4) (0.097 g, 0.12 mmol) was added and the resulting mixture was heated at 120° C. using a monomode microwave (Biotage initiator 60) with a power output ranging from 0 to 400 W for 30 minutes. The mixture was evaporated till dryness, the residue was taken up in CH₂Cl₂ and water, filtered through a short pad of Celite®. The organic layer of the filtrate was separated, washed with water, dried over MgSO₄ and evaporated till dryness. The purification was carried out by flash chromatography over silica gel (15-40 μm, 40 g, heptane/EtOAc from 95/5 to 70/30). The pure fractions were collected and the solvent was evaporated to afford 0.024 g (73%) of intermediate (14).

EXAMPLE 9

Preparation of

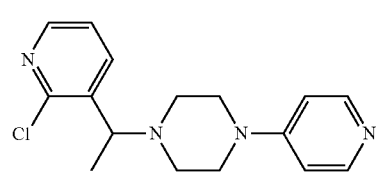

intermediate (15)

A solution of 3-acetyl-2-chloropyridine (3.40 g, 17 mmol), 1-(4-pyridyl)piperazine 3.33 g, 20.4 mmol), titanium (IV) isopropoxide (6.04 mL, 20.4 mmol) in 1,2-dichloroethane (80 mL) was heated at 50° C. 18 hours. The reaction mixture was cooled down to room temperature then sodium triacetoxyborohydride (5.4 g, 25.5 mmol) was added portionwise at room temperature. The reaction mixture was stirred at room temperature 18 hours. The reaction was poured into ice water and EtOAc was added. The mixture was filtered through a pad of Celite®, the Celite® was washed with EtOAc then the filtrate was extracted with EtOAc, dried over MgSO₄, filtered and the solvent was evaporated until dryness to afford 4.6 g of a crude product. The crude product was purified by preparative LC on (Irregular SiOH 20-45 μm 450 g MATREX), mobile phase (gradient from 0.5% NH₄OH, 95% CH₂Cl₂ 5% MeOH to 0.5% NH₄OH, 93% CH₂Cl₂, 7% MeOH). The good fractions were collected and the solvent was evaporated to yield intermediate (15).

EXAMPLE 10

Preparation of

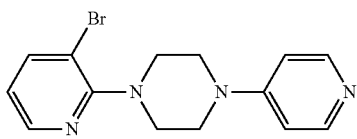

intermediate (16)

A solution of 3-bromo-2-chloropyridine (2 g, 10.4 mmol), 1-(4-pyridyl)piperazine (3.4 g, 20.8 mmol) and K₂CO₃ (3.6 g, 26 mmol) in DMF (20 mL) was heated at 120° C. for 48 hours. The mixture was poured out into water, extracted with EtOAc, the organic layer was separated, washed with water then brine, dried over MgSO₄ and evaporated till dryness to give 2.8 g of a crude product. Purification was carried out by flash chromatography over silica gel (15-40 μm. Cartridge 90 g, from CH₂Cl₂ to CH₂Cl₂/CH₃OH/NH₄OH: 95/5/0.1). The pure fractions were collected and evaporated to dryness to afford 1.9 g (57%) of intermediate (16).

EXAMPLE 11

Preparation of

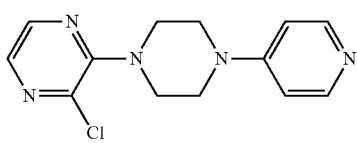

intermediate (18)

A mixture of 2,3-dichloropyrazine (4 g, 26.8 mmol), 1-(4-pyridyl)piperazine (4.4 g, 26.8 mmol) and K₂CO₃ (7.4 g, 53.7 mmol) in DMA (80 mL) was heated to 110° C. for 4 hours. The reaction mixture was cooled down to room temperature, water was added, the product was extracted with ethyl acetate, the organic layer was washed twice with water, brine, dried over MgSO₄, filtered and the solvent was evaporated to afford 4.8 g of intermediate (18) (65%).

EXAMPLE 12

Preparation of

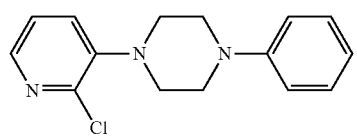

intermediate (19)

A mixture of 2-chloro-3-iodopyridine (1 g, 4.17 mmol), 1-phenylpiperazine (0.76 ml, 5.01 mmol) and sodium tert-butoxide (0.56 g, 5.8 mmol) in toluene (20 mL) was degassed with nitrogen for 10 minutes, then 9,9-dimethyl-4,5-bis(diphenylphosphino) xanthene (Xantphos) (121 mg, 0.209 mg) and tris(dibenzylideneacetone)dipalladium (Pd$_2$(dba)$_3$) (190 mg, 0.209 mmol) were added. The mixture was heated to 90° C. for 3 days. The reaction mixture was cooled down to room temperature, water was added, the product was extracted with ethyl acetate, the organic layer was washed twice with water, brine, dried over MgSO$_4$, filtered and the solvent was evaporated to afford a crude residue that was purified by flash chromatography by over silica gel (SiO60, 15-40 µm, Cartridge 50 g, from CH$_2$Cl$_2$ to CH$_2$Cl$_2$CH$_3$OH/NH$_4$OH: 97/3/0.1). The pure fractions were collected and evaporated to dryness, yielding intermediate (19) (630 mg, 55%).

B. Synthesis of the Final Compounds

Reaction scheme

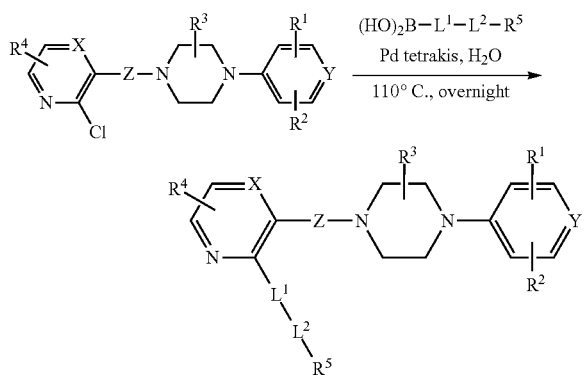

EXAMPLE 1

Preparation of

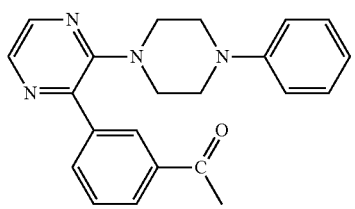

compound (1)

A mixture of 2,3-dichloropyrazine (0.15 g, 1.0 mmol), 1-phenylpiperazine (0.15 mL, 1.01 mmol) and potassium carbonate (0.42 g, 3.0 mmol) in dimethylacetamide (4 mL) was heated at 110° C. for 4 hours. The reaction mixture was cooled down to room temperature then 3-acetylbenzeneboronic acid (1.5 mmol) and water (1.5 mL) were added. The resulting mixture was purged with nitrogen for 15 minutes then tetrakis(triphenylphosphine)palladium (0.012 g, 0.010 mmol) was added and the mixture was heated to 110° C. for 18 hours. The solution was cooled down to room temperature and water was added. The organic layer was extracted with EtOAc: washed twice with brine, dried over MgSO$_4$, filtered and the solvent was evaporated to afford 0.33 g of crude product. Purification was carried out by preparative LC on (Stability Silica 5 µm 150×30.0 mm). Mobile phase (gradient from 3% ethyl acetate, 97% heptane, 0% MeOH to 100% ethyl acetate, 0% heptane, 0% MeOH). The pure fractions were collected and the solvent was evaporated to afford 0.139 g of awaited compound. The residue was crystallized from diethylether, filtered off and dried under vacuum at 60° C. to give 0.146 g of compound (1) (35%).

EXAMPLE 2

Preparation of

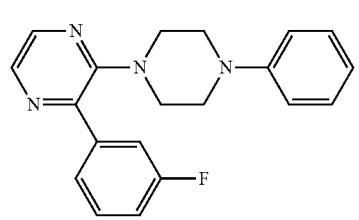

compound (6)

A mixture of 2,3-dichloropyrazine (0.15 g, 1.0 mmol), 1-phenylpiperazine (0.15 mL, 1.01 mmol) and potassium carbonate (0.42 g, 3.0 mmol) in dimethylacetamide (4 mL) was heated at 110° C. for 4 hours. The reaction mixture was cooled down to room temperature; then 3-fluorobenzeneboronic acid (0.155 g, 1.5 mmol) and water (1.5 mL) were added. The resulting mixture was purged with nitrogen for 15 minutes then tetrakis(triphenylphosphine)-palladium (0.012 g, 0.010 mmol) was added and the mixture was heated to 110° C. for 18 hours. The solution was cooled down to room temperature and water was added. The organic layer was extracted with EtOAc; washed twice with brine, dried over MgSO$_4$, filtered and the solvent was evaporated to afford 0.33 g of crude product. Purification was carried out by preparative LC on (Stability Silica 5 µm 150×30.0 mm), mobile phase (gradient from 3% ethyl acetate, 97% heptane, 0% MeOH to 100% ethyl acetate, 0% heptane, 0% MeOH). The pure fractions were collected and the solvent was evaporated to afford 0.139 g of awaited compound. The residue was crystallized from diethylether, filtered off and dried under vacuum at 60° C. to give 0.044 g (13%) of compound (6) as a white powder.

$^1$H NMR (500 MHz, DMSO-d$_6$) δ 8.24 (s, 2H), 7.80 (d, J=7.9 Hz, 1H), 7.72 (d, J=10.1 Hz, 1H), 7.55 (q, J=7.9 Hz, 1H), 7.25-7.33 (m, 1H), 7.21 (t, J=7.7 Hz, 2H), 6.94 (d, J=7.7 Hz, 2H), 6.79 (t, J=7.7 Hz, 1H), 3.22-3.30 (m, 4H), 3.12-3.20 (m, 4H).

Compound (7) was prepared analogously starting from 2,3-dichloropyrazine, 1-(4-pyridyl)piperazine and benzofuran-5-ylboronic acid. Yield: 0.023 g (10%).

EXAMPLE 3

Preparation of

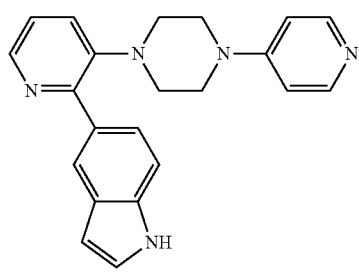

compound (36)

A solution of intermediate (1) (0.2 g, 0.73 mmol) and 5-(4,4,5,5,-tetramethyl-1,3,2-dioxaborolan-2-yl)-1H-indole (0.41 g, 1.67 mmol) in potassium carbonate solution 2M (0.9 mL) and DME (3 mL) was purged with nitrogen for 5 minutes then tetrakis (triphenylphosphine)-palladium (0.084 g, 0.073 mmol) was added portionwise. The mixture was heated at 100° C. using a single mode microwave (Biotage initiator60) with a power output ranging from 0 to 400 W for 45 min. Water and EtOAc were added. The organic layer was extracted, dried over $MgSO_4$, filtered and evaporated to give 0.6 g of crude product. Purification was carried out by preparative LC (Stationary phase: Sunfire Silica 5 μm 150× 30.0 mm). Mobile phase: Gradient from 0.2% $NH_4OH$, 98% $CH_2Cl_2$, 2% MeOH to 1% $NH_4OH$, 90% $CH_2Cl_2$, 10% MeOH). Pure fractions were collected and evaporated to give 0.17 g of product. The residue was crystallized from DIPE, filtered off and dried under vacuum at 60° C. yielding compound (36) as a white powder, 0.125 g, 48%.

$^1$H NMR (500 MHz. DMSO-$d_6$) δ 11.15 (br. s., 1H), 8.29 (d, J=4.1 Hz, 1H), 8.19 (s, 1H), 8.13 (d, J=6.0 Hz, 2H), 7.81 (d, J=8.2 Hz, 1H), 7.46 (d, J=8.0 Hz, 1H), 7.42 (d, J=8.2 Hz, 1H), 7.35 (br. s., 1H), 7.24 (dd, J=4.1, 8.0 Hz, 1H), 6.79 (d, J=6.0 Hz, 2H), 6.48 (br. s., 1H), 3.25-3.32 (m, 4H), 2.86-2.98 (m, 4H).

EXAMPLE 4

Preparation of compound (40)

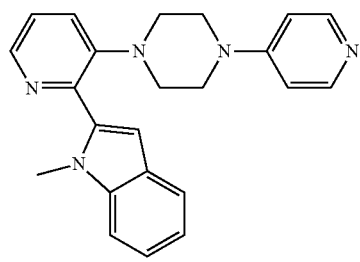

A solution of intermediate (1) (0.2 g, 0.73 mmol) and 1-methyl-2-indoleboronic acid pinacol ester (0.43 g, 1.67 mmol) in potassium carbonate solution 2M (0.73 mL) and DME (3 mL) was purged with nitrogen for 5 minutes then tetrakis (triphenylphosphine) palladium (0.084 g, 0.073 mmol) was added portionwise. The mixture was heated at 100° C. using a single mode microwave (Biotage initiator 60) with a power output ranging from 0 to 400 W for 45 minutes. Water and EtOAc were added. The organic layer was extracted, dried over $MgSO_4$, filtered and evaporated to give 0.6 g of crude product. Purification was carried out by preparative LC (Stationary phase: 35-40 μm, 24 g, Grace Resolv), mobile phase: gradient from $CH_2Cl_2$ 100% to $CH_2Cl_2$/MeOH/$NH_4OH$ 95/5/0.5). Pure fractions were collected and evaporated to give 0.22 g of product. The residue was crystallized from DIPE, filtered off and dried under vacuum at 60° C. yielding compound (40) as a white powder, 0.194 g (72%).

$^1$H NMR (400 MHz, DMSO-$d_6$) δ 8.35 (d, J=4.1 Hz, 1H), 8.12 (d, J=6.1 Hz, 2H), 7.58 (m, 2H), 7.50 (d, J=8.1 Hz, 1H), 7.39 (dd, J=4.1, 8.1 Hz, 1H), 7.19 (t, J=7.6 Hz, 1H), 7.06 (t, J=7.6 Hz, 1H), 6.90 (s, 1H), 6.76 (d, J=6.1 Hz, 2H), 3.75 (s, 3H), 3.20-3.27 (m, 4H), 2.90-3.00 (m, 4H).

Other compounds as listed in Table A-1 were prepared in an analogous way by reacting intermediate (1) with either phenylboronic acid, (4-methylthio)phenylboronic acid, 4-methoxyphenylboronic acid, 1H-indole-7-boronic acid pinacol ester, 3-chlorophenyl-boronic acid, 3,4-(methylenedioxy)phenylboronic acid, 2,4-dichlorophenylboronic acid, 3,4-dichlorophenylboronic acid, 3-fluorophenylboronic acid, 4-fluorophenyl-boronic acid, 3,4-dimethoxyphenylboronic acid, 2-methoxypyridine-5-boronic acid pinacol ester, 2-methoxypyridine-4-boronic acid, 6-isopropoxypyridine-3-boronic acid pinacol ester, 4-(4,4,5,5-tetramethyl-1,3,2-dioxaborolan-2-yl)pyridine, (2,3-dihydro-1,4-benzodioxin-6-yl)boronic acid, benzo[b]thiophene-2-boronic acid, 4-trifluoro-methoxyphenylboronic acid, 2-(benzofuran-5-yl)-4,4,5,5-tetramethyl-[1,3,2]dioxa-borolane, 3-cyanophenylboronic acid, 2,3-dihydrobenzo[b]furan-5-boronic acid, 3-quinolineboronic acid, 5-quinolineboronic acid, 4-(dimethylamino)phenylboronic acid, (4-methylthio)phenylboronic acid, 7-(4,4,5,5-tetramethyl-1,3,2-dioxaborolan-2-yl) indole, 4-(4,4,5,5-tetramethyl-[1,3,2]dioxaborolan-2-yl)-1H-indole. N-[4-(4,4,5,5-tetramethyl-1,3,2-dioxaborolan-2-yl)phenyl]methane-sulfonamide, 6-(4,4,5,5-tetramethyl-1,3,2-dioxaborolan-2-yl)benzo[d]thiazole or 2-(benzo[b]furan-3-yl)-4,4,5,5-tetramethyl-[1,3,2]dioxaborolane.

EXAMPLE 5

Preparation of compound (41)

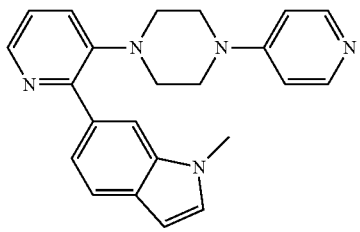

A solution of intermediate (1) (0.2 g, 0.73 mmol) and 1-methyl-1H-indole-6-boronic acid pinacol ester (0.43 g, 1.67 mmol) in potassium carbonate solution 2M (0.73 mL) and DME (3 mL) was purged with nitrogen for 5 minutes then tetrakis (triphenyl-phosphine)palladium (0.084 g, 0.073 mmol) was added portionwise. The mixture was heated at 100° C. using a single mode microwave (Biotage initiator 60) with a power output ranging from 0 to 400 W for 45 minutes. Water and EtOAc were added. The organic layer was extracted, dried over $MgSO_4$, filtered and evaporated to give 0.50 g of crude product. Purification was carried out by preparative LC (Stationary phase: irregular 15-40 μm 30 g Merck), mobile phase: 0.5%/o $NH_4OH$, 95% $CH_2Cl_2$, 5% MeOH). Pure fractions were collected and evaporated to give 0.05 g of awaited product. The residue was freeze-dried with acetonitrile/water 20/80 to give compound (41) as a white powder (0.042 g, 15%).

$^1$H NMR (500 MHz, DMSO-$d_6$) δ 8.32 (dd, J=1.3, 4.7 Hz, 1H), 8.13 (d, J=6.3 Hz, 2H), 8.06 (s, 1H), 7.79 (dd, J=1.3, 8.2 Hz, 1H), 7.58 (d, J=8.2 Hz, 1H), 7.50 (dd, J=1.3, 8.2 Hz, 1H), 7.37 (d, J=2.5 Hz, 1H), 7.28 (dd, J=4.7, 8.2 Hz, 1H), 6.80 (d, J=6.3 Hz, 2H), 6.43 (d, J=2.5 Hz, 1H), 3.81 (s, 3H), 3.28-3.32 (m, 4H), 2.91-2.96 (m, 4H).

Compound (10) was prepared analogously using intermediate (1) and 2-naphtha-leneboronic acid. Yielding: 0.063 g (34%).

Compound (23) was prepared analogously using intermediate (1) and benzofuran-2-boronic acid. Yield: 0.066 g (34%).

Compound (24) was prepared analogously using intermediate (1) and 1-methyl-5-(4,4,5,5-tetramethyl-1,3,2-dioxaborolan-2-yl)-1H-indole. Yield: 0.128 g (52%).

Compound (26) was prepared analogously using intermediate (1) and 1-naphta-leneboronic acid. Yield: 0.21 g (79%).

EXAMPLE 6

Preparation of compound (44)

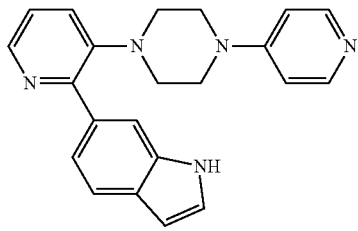

Compound (44) was prepared in an analogous way as compound (41) starting from intermediate (1) and indole-6-boronic acid pinacolester. Yield: 0.16 g (62%).

EXAMPLE 7

Preparation of compound (74)

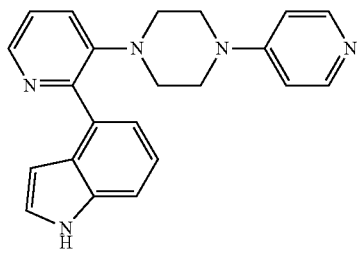

A solution of intermediate (1) (0.2 g, 0.73 mmol) and 1-H-indole-4-boronic acid pinacol ester (0.407 g, 1.67 mmol) in potassium carbonate solution 2M (0.73 mL) and DME (3 mL) was purged with nitrogen for 5 minutes then tetrakis (triphenylphosphine) palladium (0.084 g, 0.073 mmol) was added portionwise. The mixture was heated at 100° C. using a single mode microwave (Biotage initiator60) with a power output ranging from 0 to 400 W for 45 minutes. Water and EtOAc were added. The organic layer was extracted, dried over MgSO$_4$, filtered and evaporated to give 0.6 g of crude product. Purification was carried out by preparative LC (stationary phase: irregular 15-40 m 30 g Merck), mobile phase: 0.5% NH$_4$OH, 95% CH$_2$Cl$_2$, 5% MeOH). Pure fractions were collected and evaporated to give 0.16 g of residue. The residue was crystallized from DIPE, filtered off and dried under vacuum at 60° C. affording compound (74) as a white powder (0.142 g, 55%).

$^1$H NMR (500 MHz, DMSO-d$_6$) δ 11.08 (br. s., 1H), 8.30 (dd, J=1.1, 4.6 Hz, 1H), 8.09 (d, J=6.3 Hz, 2H), 7.50 (dd, J=1.1, 8.2 Hz, 1H), 7.42 (d, J=7.0 Hz, 1H), 7.38 (d, J=7.0 Hz, 1H), 7.28-7.35 (m, 2H), 7.16 (t, J=7.0 Hz, 1H), 6.71 (d, J=6.3 Hz, 2H), 6.35 (br. s., 1H), 2.99-3.08 (m, 4H), 2.81-2.89 (m, 4H)

EXAMPLE 8

Preparation of compound (48)

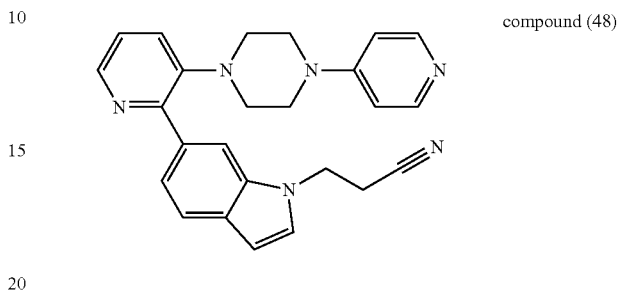

Sodium hydride 60% (45 mg, 1.125 mmol) was added portionwise to a solution of compound (44) (200 mg, 0.563 mmol) in DMF (4 mL) at 5° C. under nitrogen atmosphere. The reaction mixture was stirred at 5° C. for 30 minutes then a solution of 3-bromopropionitrile (0.0934 mL, 1.125 mmol) was added dropwise at 5° C. The reaction mixture was stirred at 5° C. for 1 hour then overnight at room temperature. The reaction mixture was poured into ice water and CH$_2$Cl$_2$ was added. The organic layer was separated, washed with brine, dried over MgSO$_4$, evaporated until dryness to afford 0.28 g of a crude product. Purification was carried out by preparative LC (stationary phase: Spherical bare silica 5 μm 150×30.0 mm), mobile phase: gradient from 0% NH$_4$OH, 100% CH$_2$Cl$_2$, 0% MeOH to 0.7% NH$_4$OH, 93% CH$_2$Cl$_2$, 7% MeOH). The pure fractions were collected and the solvent were evaporated to afford 100 mg of the expected product. The residue was crystallized from DIPE, filtered and dried under vacuum at 60° C. to afford 46 mg of compound (48), 20%.

$^1$H NMR (500 MHz, DMSO-d$_6$) δ 8.33 (dd, J=1.4, 4.6 Hz, 1H), 8.08-8.16 (m, 3H), 7.78 (dd, J=1.4, 8.4 Hz, 1H), 7.60 (d, J=8.4 Hz, 1H), 7.51 (dd, J=1.4, 8.0 Hz, 1H), 7.49 (d, J=3.1 Hz, 1H), 7.29 (dd, J=4.6, 8.0 Hz, 1H), 6.79 (d, J=3.8 Hz, 2H), 6.51 (d, J=3.1 Hz, 1H), 4.52 (t, J=6.5 Hz, 2H), 3.26-3.31 (m, 4H), 3.03 (t, J=6.5 Hz, 2H), 2.86-2.97 (m, 4H).

EXAMPLE 9

Preparation of compound (51)

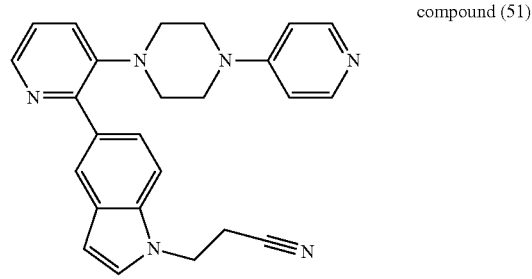

Compound (51) was prepared in the same way as compound (48) starting from compound (36) and 3-bromopropionitrile. Yield: 0.058 g (25%).

EXAMPLE 10

Preparation of

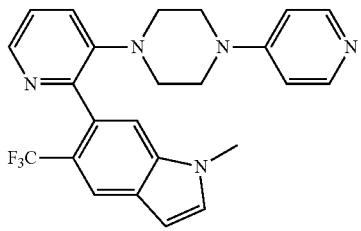

compound (49)

A solution of intermediate (1) (65 mg, 0.237 mmol) and intermediate (3) (176.92 mg, 0.544 mmol) in potassium carbonate solution 2M (0.237 mL) and DME (1.50 mL) was purged with nitrogen for 5 minutes then tetrakis(triphenyl-phosphine)palladium(0) (27.34 mg, 0.0237 mmol) was added portionwise. The mixture was heated at 100° C. using a singlemode microwave (Biotage initiator60) with a power output ranging from 0 to 400 W for 50 minutes. Water and $CH_2Cl_2$ were added. The organic layer was extracted, dried over $MgSO_4$, filtered and evaporated. The crude product was purified by preparative LC (stationary phase: X-Bridge-C18 5 μm 30*150 mm), mobile phase: gradient from 50% $NH_4HCO_3$ 0.5%, 50% MeOH to 20% $NH_4HCO_3$ 0.5%, 80% MeOH). The pure fractions were collected and the solvent was evaporated to afford 0.022 g of the desired product, it was lyophilized with acetonitrile/water (80/20) to afford compound (49) (0.020 g, 19%).
$^1$H NMR (500 MHz, DMSO-$d_6$) δ 8.27 (dd, J=1.4, 4.7 Hz, 1H), 8.08 (d, J=6.6 Hz, 2H), 7.94 (s, 1H), 7.73 (s, 1H), 7.58 (d, J=2.8 Hz, 1H), 7.55 (dd, J=1.4, 8.0 Hz, 1H), 7.35 (dd, J=4.7, 8.0 Hz, 1H), 6.72 (d, J=6.6 Hz, 2H), 6.56 (d, J=2.8 Hz, 1H), 3.91 (s, 3H), 2.97-3.09 (m, 4H), 2.77-2.91 (m, 4H).

EXAMPLE 11 a) Preparation of intermediate (4)

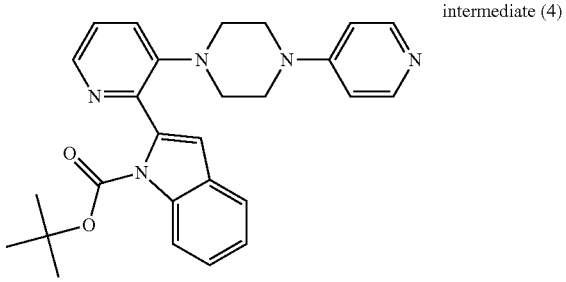

A solution of intermediate (1) (5 g, 18.2 mmol) and N-Boc-protected 1H-indole-2-boronic acid (10.93 g, 41.86 mmol) in potassium carbonate solution 2M (18.2 mL) and DME (80 mL) was purged with nitrogen for 5 minutes then tetrakis(triphenyl-phosphine)-palladium(0) (2.1 g, 1.82 mmol) was added portionwise. The mixture was heated at 80° C. overnight. The reaction mixture was cooled down to room temperature. Water and EtOAc were added. The organic layer was extracted, dried over $MgSO_4$, filtered and evaporated. The crude product was triturated from $CH_2Cl_2$, filtered and dried under vacuum at room temperature to afford a first fraction of the desired compound (2.4 g, 29%6). The filtrate was evaporated until dryness and purified by preparative LC (stationary phase: Sunfire Silica 5 μm 150× 30.0 mm), mobile phase: gradient from DCM 100% to 90% $NH_4OH$, 10% $CH_2Cl_2$, 1% MeOH). The pure fractions were collected and the solvent was evaporated to afford intermediate (4) (2.6 g, 31%).

b) Preparation of compound (47)

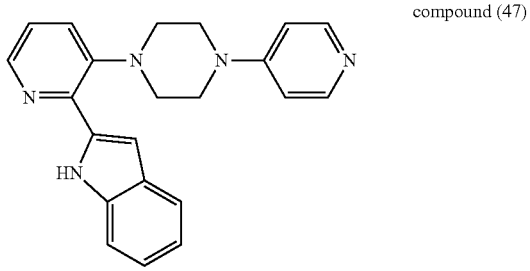

Trifluoroacetic acid (4.01 mL, 54 mmol) was added dropwise to a solution of intermediate (4) (1.23 g, 2.7 mmol) in $CH_2Cl_2$ (20 mL) at room temperature. The reaction mixture was stirred at room temperature overnight. The mixture was evaporated until dryness. The residue was taken up with $CH_2Cl_2$ and ice water. The mixture was basified with a solution of NaOH 3N then the organic layer was separated, washed with brine, dried over $MgSO_4$, filtered and evaporated until dryness to afford 1 g of the desired compound. It was triturated from $Et_2O$, filtered and dried under vacuum at room temperature to afford compound (47) (0.90 g, 93%).

EXAMPLE 12

Preparation of compound (50)

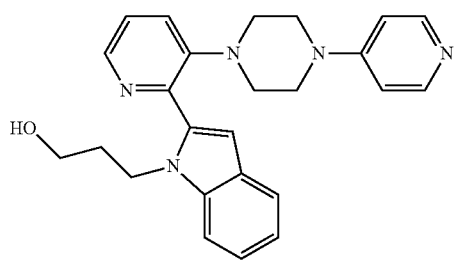

Step 1:
Sodium hydride 60% (45 mg, 1.125 mmol) was added portionwise to a solution of compound (47) (200 mg, 0.563 mmol) in DMF (4 mL) at 5° C. under nitrogen atmosphere. The reaction mixture was stirred at 5° C. for 30 minutes then (3-bromo-propoxy)-tert-butyldimethylsilane (0.269 mL, 1.125 mmol) was added dropwise at 5° C. The reaction mixture was stirred at 5° C. for 1 hour then overnight at room temperature. The reaction mixture was poured into ice water and $CH_2Cl_2$ was added. The organic layer was separated, washed with brine, dried over $MgSO_4$, evaporated until dryness. The resulting product was used in the next step without further purification.

Step 2:

A solution of tetrabutylammonium fluoride 1 M (0.6 ml, 0.604 mmol) was added dropwise to a solution of the product of step 1 (0.29 g, 0.549 mmol) in CH$_2$Cl$_2$ (5 mL) at room temperature. The reaction mixture was stirred at room temperature overnight. The reaction mixture was poured into ice water and CH$_2$Cl$_2$ was added. The organic layer was separated, washed with brine, dried over MgSO$_4$, filtered and the solvent was evaporated until dryness. The crude product was purified by preparative LC (stationary phase: irregular bare silica 40 g), mobile phase: 0.5% NH$_4$OH, 95% CH$_2$Cl$_2$, 5% MeOH). The desired fractions were collected, the solvent was evaporated and the resulting residue was crystallized from DIPE, filtered and dried under vacuum at 60° C. to afford compound (50) (0.050 g, 22%).

$^1$H NMR (400 MHz, DMSO-d$_6$) δ 8.34 (d, J=4.5 Hz, 1H), 8.12 (d, J=5.6 Hz, 2H), 7.47-7.66 (m, 3H), 7.38 (dd, J=4.5, 8.1 Hz, 1H), 7.17 (t, J=7.6 Hz, 1H), 7.04 (t, J=7.6 Hz, 1H), 6.96 (s, 1H), 6.79 (d, J=5.6 Hz, 2H), 4.35-4.51 (m, 3H), 3.18-3.30 (m, 6H), 2.90-3.03 (m, 4H), 1.67 (quin, J=6.6 Hz, 2H).

EXAMPLE 13

Preparation of

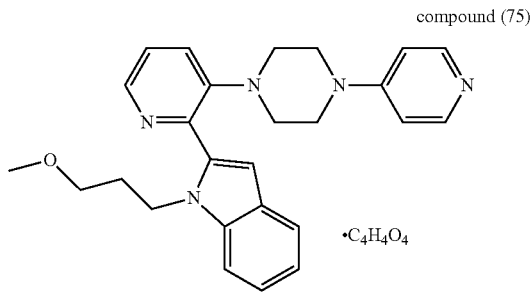

compound (75)

Sodium hydride 60% (45 mg, 1.125 mmol) was added portionwise to a solution of compound (47) (200 mg, 0.563 mmol) in DMF (4 ml) at 5° C. under nitrogen atmosphere. The reaction mixture was stirred at 5° C. for 30 minutes then a solution of 1-bromo-3-methoxypropane (0.126 ml, 1.125 mmol) was added dropwise at 5° C. The reaction mixture was stirred at 5° C. for 1 hour then overnight at room temperature. The reaction mixture was poured into ice water and CH$_2$Cl$_2$ was added. The organic layer was separated, washed with brine, dried over MgSO$_4$, evaporated until dryness. The crude product was purified by preparative LC (stationary phase: irregular bare silica 40 g), mobile phase: 0.5% NH$_4$OH, 95% CH$_2$Cl$_2$, 5% MeOH). The desired fractions were collected, the solvent was evaporated and the residue was dissolved in acetone then 3 equivalents (0.105 g) of fumaric acid was added portionwise at room temperature, the reaction was stirring at room temperature for 1 hour. The filtrate was filtered, washed with acetone, dried under vacuum at 60° C. to afford compound (75) (130 mg, 41%).

$^1$H NMR (500 MHz, DMSO-d$_6$) δ 11.74-13.91 (m, 1H), 8.35 (d, J=5.0 Hz, 1H), 8.13 (d, J=6.3 Hz, 2H), 7.59 (d, J=7.9 Hz, 1H), 7.56 (d, J=7.9 Hz, 1H), 7.51 (d, J=7.9 Hz, 1H), 7.38 (dd, J=5.0, 7.9 Hz, 1H), 7.18 (t, J=7.9 Hz, 1H), 7.05 (t, J=7.9 Hz, 1H), 6.97 (s, 1H), 6.83 (d, J=6.3 Hz, 2H), 6.60 (s, 2H), 4.43 (t, J=6.9 Hz, 2H), 3.28-3.33 (m, 4H), 3.10 (t, J=6.9 Hz, 2H), 3.05 (s, 3H), 2.90-2.99 (m, 4H), 1.74 (quin. J=6.9 Hz, 2H).

EXAMPLE 14

Preparation of

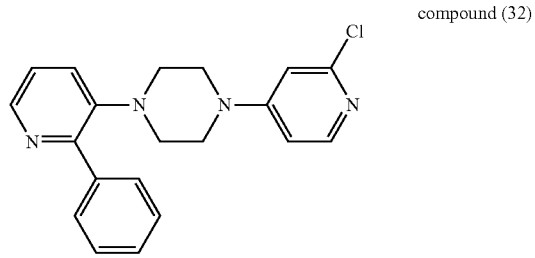

compound (32)

A mixture of intermediate (7) (0.25 g, 1.04 mmol), 2-chloro-4-iodopyridine (0.3 g, 1.25 mmol), sodium tert-butoxide (0.14 g, 1.46 mmol), 9,9-dimethyl-4,5-bis(diphenyl-phosphino)Xanthen (0.03 g, 0.05 mmol) and tris(dibenzylideneacetone)palladium (0.024 g, 0.026 mmol) in toluene (5 mL) was heated at 110° C. overnight. The reaction mixture was cooled down to room temperature, poured into water and EtOAc, filtered through a pad of Celite®. The filtrate was decanted, the organic layer was washed with brine, dried over MgSO$_4$, filtered and the solvent was evaporated. Purification was carried out by preparative LC on (Spherical SiOH 10 μm 60 g PharmPrep MERCK), mobile phase (0.05% NH$_4$OH, 99% DCM, 1% isopropanol). The pure fractions were collected, the solvent was evaporated and the residue was taken up in Et$_2$O, filtered off and dried under vacuum at 60° C. to afford 0.066 g (18%) of compound (32).

$^1$H NMR (500 MHz, DMSO-d$_6$) δ 8.32 (d, J=4.4 Hz, 1H), 7.98 (d, J=7.25 Hz, 2H), 7.94 (d, J=6.0 Hz, 1H), 7.52 (d, J=8.2 Hz, 1H), 7.42-7.48 (m, 2H), 7.35-7.41 (m, 1H), 7.32 (dd, J=4.4, 8.2 Hz, 1H), 6.82-6.89 (m, 2H), 3.34-3.40 (m, 4H), 2.85-2.94 (m, 4H).

Compound (29) was analogously starting from intermediate (7) and 4-bromo-2-methoxypyridine. Yield: 0.092 g (35%).

EXAMPLE 15

Preparation of

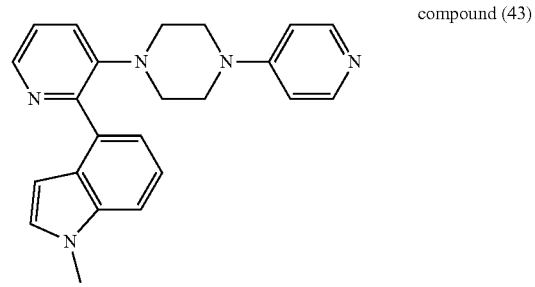

compound (43)

Sodium hydride 60%6 (0.038 g, 0.957 mmol) was added portionwise to a solution of compound (74) (0.17 g, 0.478 mmol) in DMF (2 mL) at 5° C. under nitrogen atmosphere. The reaction mixture was stirred at 5° C. for 30 minutes then a solution of iodomethane (0.06 mL, 0.957 mmol) was added dropwise at 5° C. for 1 hour. The resulting solution was stirred at room temperature overnight. The reaction mixture was poured into ice water and EtOAc was added. The organic layer was separated, washed with brine, dried over MgSO$_4$, filtered and the solvent was evaporated until dryness to afford 0.23 g of crude product. Purification was carried out by preparative LC (35-40 μm, 12 g, Grace Resolv), mobile phase: gradient from CH$_2$Cl$_2$ 100% to CH$_2$Cl$_2$ 95%/MeOH 5%/NH$_4$OH 0.50%). The pure fractions were collected, the solvent was evaporated and the residue was crystallized from DIPE, filtered off and dried under vacuum at 60° C. to give compound (43) as a white powder (0.136 g, 77%).

$^1$H NMR (500 MHz, DMSO-d$_6$) δ 8.30 (dd, J=1.3, 4.4 Hz, 1H), 8.10 (d, J=6.3 Hz, 2H), 7.51 (dd, J=1.3, 8.2 Hz, 1H), 7.42-7.49 (m, 2H), 7.32 (dd, J=4.4, 8.2 Hz, 1H), 7.29 (d, J=2.8 Hz, 1H), 7.23 (t, J=7.7 Hz, 1H), 6.72 (d, J=6.3 Hz, 2H), 6.36 (d, J=2.8 Hz, 1H), 3.81 (s, 3H), 3.03-3.08 (m, 4H), 2.82-2.88 (m, 4H).

EXAMPLE 16

Preparation of

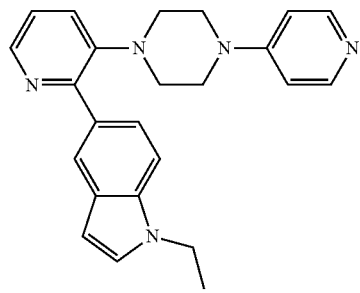

compound (37)

Sodium hydride 60% (0.022 g, 0.56 mmol) was added portionwise to a solution of compound (36) (0.1 g, 0.28 mmol) in DMF (2 mL) at 5° C. under nitrogen atmosphere. The reaction mixture was stirred at 5° C. for 30 minutes then a solution of iodoethane (0.045 mL, 0.56 mmol) was added dropwise at 5° C. for 1 hour. The resulting solution was stirred at room temperature for 2 hours. The reaction mixture was poured into ice water and EtOAc was added. The organic layer was separated, washed with brine, dried over MgSO$_4$, filtered and the solvent was evaporated until dryness to afford 0.09 g of crude product. Purification was carried out by preparative LC (Stationary phase: Irregular SiOH 15-40 μm, 10 g, Merck), mobile phase: CH$_2$Cl$_2$ 100% to CH$_2$Cl$_2$ 95/MeOH 5/NH$_4$OH 0.5. The pure fractions were collected, the solvent was evaporated and the residue was crystallized from DIPE, filtered off and dried under vacuum at 60° C. to give compound (37) as a white powder (0.039 g, 36%).

$^1$H NMR (500 MHz. DMSO-d$_6$) δ 8.30 (d, J=4.4 Hz, 1H), 8.23 (s, 1H), 8.13 (d, J=6.3 Hz, 2H), 7.86 (d, J=8.7 Hz, 1H), 7.51 (d, J=8.7 Hz, 1H), 7.48 (d, J=8.2 Hz, 1H), 7.40 (d, J=3.1 Hz, 1H), 7.25 (dd, J=4.4, 8.2 Hz, 1H), 6.80 (d, J=6.3 Hz, 2H), 6.49 (d, J=3.1 Hz, 1H), 4.22 (q, J=7.3 Hz, 2H), 3.26-3.33 (m, 4H), 2.88-2.98 (m, 4H), 1.39 (t, J=7.3 Hz, 3H).

EXAMPLE 17

Preparation of

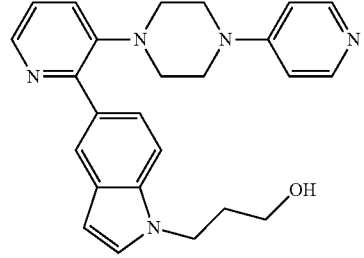

compound (46)

Step 1

Sodium hydride 60% (0.045 g, 1.125 mmol) was added portionwise to a solution of compound (36) (0.2 g, 0.563 mmol) in DMF (4 mL) at 5° C. under nitrogen atmosphere. The reaction mixture was stirred at 5° C. for 30 minutes then a solution of (3-bromo-propoxy)-tert-butyldimethylsilane (0.269 mL, 1.125 mmol) was added dropwise at 5° C. for 1 hour. The resulting solution was stirred at room temperature overnight. The reaction mixture was poured into ice water and CH$_2$Cl$_2$ was added. The organic layer was separated, washed with brine, dried over MgSO$_4$, filtered and the solvent was evaporated until dryness to afford 0.405 g of crude product. Purification was carried out by preparative LC (Stationary phase: 30 μm, 25 g, Interchim), mobile phase: CH$_2$Cl$_2$ 100% to CH$_2$Cl$_2$ 90%/MeOH10%/NH$_4$OH 0.5%). The pure fractions were collected and the solvent was evaporated to the product used for the next step.

Step 2

A solution of tetrabutylammonium fluoride (0.512 mL, 0.512 mmol) was added dropwise to a solution of the product of step 1 (0.18 g, 0.341 mmol) in THF (2 mL) at room temperature. The reaction mixture was stirred at room temperature overnight. The reaction mixture was poured into ice water and EtOAc was added. The mixture was basified with an aqueous saturated solution of NaHCO$_3$ 10% then the organic layer was separated, washed with brine, dried over MgSO$_4$, filtered and the solvent was evaporated until dryness to afford 0.16 g of crude product. Purification was carried out by preparative LC (35-40 μm, 12 g, Grace Resolv), mobile phase: gradient from CH$_2$Cl$_2$ 100% to CH$_2$Cl$_2$ 95%/MeOH 5%/NH$_4$OH 0.50%). The pure fractions were collected, the solvent was and the residue was triturated from DIPE, filtered off and dried under vacuum at 60° C. to give compound (46) as a white powder (0.067 g, 47%).

$^1$H NMR (500 MHz, DMSO-d$_6$) δ 8.30 (dd, J=1.3, 4.7 Hz, 1H), 8.22 (s, 1H), 8.13 (d, J=6.6 Hz, 2H), 7.86 (dd, J=1.3, 8.5 Hz, 1H), 7.50 (d, J=8.5 Hz, 1H), 7.48 (dd, J=1.3, 8.2 Hz, 1H), 7.36 (d, J=3.2 Hz, 1H), 7.25 (dd, J=4.7, 8.2 Hz, 1H), 6.80 (d, =6.6 Hz, 2H), 6.49 (d, J=3.2 Hz, 1H), 4.63 (t, J=6.0 Hz, 1H), 4.24 (t. J=6.0 Hz, 2H), 3.41 (q, J=6.0 Hz, 2H), 3.27-3.32 (m, 4H), 2.90-2.97 (m, 4H), 1.91 (quin, J=6.0 Hz, 2H).

EXAMPLE 18

Preparation of compound (52)

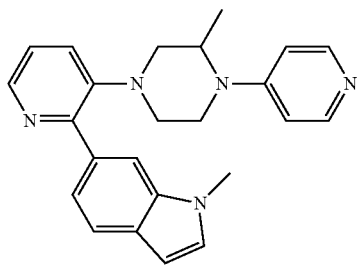

A mixture of intermediate (9) (100 mg, 0.32 mmol), 4-iodo pyridine (80 mg, 0.39 mmol), sodium tert-butoxide (44 mg, 0.45 mmol), 9,9-dimethyl-4,5-bis(diphenylphosphino)Xanthen (10 mg, 0.016 mmol) and tris(dibenzylideneacetone)palladium (7.4 mg, 0.008 mmol) in toluene (3 mL) was heated at 110° C. for 36 hours. The mixture was poured out into water, extracted with EtOAc, the mixture was filtered through a short pad of Celite®, the organic layer was separated, washed with water and brine, dried (MgSO$_4$) and evaporated till dryness to afford 190 mg of a crude product. Purification was carried out by preparative LC (stationary phase: irregular bare silica 40 g), mobile phase: 0.5% NH$_{40}$H, 96% CH$_2$Cl$_2$, 4% CH$_2$Cl$_2$). The pure fractions were collected and the solvent was evaporated to afford 18 mg (14%) of compound (52) as an oil.

$^1$H NMR (500 MHz, DMSO-d$_6$) δ 8.33 (dd, J=1.3, 4.7 Hz, 1H), 8.10 (d, J=6.6 Hz, 2H), 7.97 (s, 1H), 7.64 (dd, J=1.3, 8.2 Hz, 1H), 7.60 (d, J=8.2 Hz, 1H), 7.52 (dd, J=1.3, 8.0 Hz, 1H), 7.38 (d, J=2.8 Hz, 1H), 7.30 (dd, J=4.7, 8.0 Hz, 1H), 6.72 (d, J=6.6 Hz, 2H), 6.45 (d, J=2.8 Hz, 1H), 4.22-4.32 (m, 1H), 3.8 (s, 3H), 3.41-3.44 (m, 1H), 3.06-3.20 (m, 2H), 2.96 (dd, J=3.5, 11.3 Hz, 1H), 2.79 (dt, J=3.5, 12.2 Hz, 1H), 2.42-2.48 (m, 1H-partially obscured by solvent peak), 1.10 (d, J=6.6 Hz, 3H).

EXAMPLE 19

Preparation of compound (68)

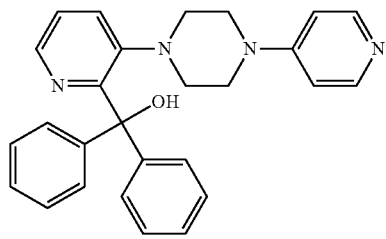

Phenylmagnesium chloride (0.89 mL, 1.60 mmol) was added dropwise to a solution of intermediate (10) (200 mg, 0.64 mmol) in THF (2 mL) at 0° C. The reaction mixture was stirred at 0° C. for 1 hour, then slowly warmed to room temperature and stirred 1 hour. The reaction mixture was poured into a solution of NH$_4$Cl saturated, extracted with AcOEt. The organic layer was dried over MgSO$_4$, filtered and the solvent evaporated till dryness to give 0.25 g of the crude product. Purification of the crude product was carried out by flash chromatography over silica gel (30 μm, Cartridge 12 g. from CH$_2$Cl$_2$ to CH$_2$Cl$_2$/CH$_3$OH/NH$_4$OH: 95/5/0.1). The pure fractions were collected and the solvent was evaporated to dryness to afford 0.125 g of a product which was taken up in DIPE, filtered off and dried (60° C., vacuum) to give 0.102 g (38%) of compound (68).

$^1$H NMR (500 MHz. DMSO-d$_6$) δ 8.81 (s, 1H), 8.34 (dd, J=1.4, 4.6 Hz, 1H), 8.16 (d, J=6.3 Hz, 2H), 8.04 (dd, J=1.4, 8.0 Hz, 1H), 7.39 (dd, J=4.6, 8.0 Hz, 1H), 7.20-7.32 (m, 10H), 6.82 (d, J=6.3 Hz, 2H), 3.09-3.39 (m, 4H), 2.61-2.72 (m, 4H).

Compound (70) was prepared analogously starting from compound (68) and methylmagnesium bromide. Yield: 0.044 g (23%).

EXAMPLE 20

Preparation of compound (64)

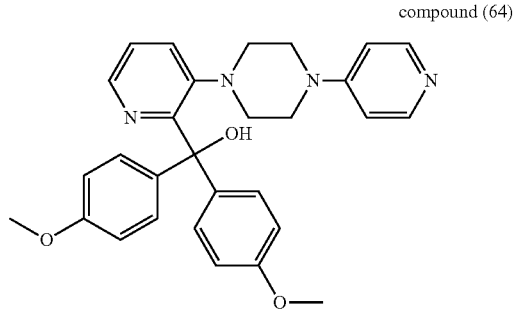

4-Methoxyphenylmagnesium bromide, 1M solution in THF (0.32 mL, 0.32 mmol) was added dropwise to a solution of intermediate (10) (100 mg, 0.32 mmol) in THF (1 mL) at 0° C. The reaction mixture was stirred at 0° C. for 1 hour, then slowly warmed to room temperature and stirred 1 hour. Additional amount of 4-methoxyphenylmagnesium bromide, 1M solution in THF was added (0.32 mL, 0.32 mmol) at 0° C. and the reaction mixture was stirred overnight at room temperature. The reaction mixture was poured into a solution of NH$_4$Cl saturated, extracted with AcOEt. The organic layer was dried over MgSO$_4$, filtered and evaporated to dryness to give 0.15 g of the crude product. Purification of the crude product was carried out by CH$_2$Cl$_2$ to CH$_2$Cl$_2$/CH$_3$OH/NH$_4$OH:95/5/0.1. The pure fractions were collected, evaporated to dryness and the residue was freeze-dried dried with acetonitrile/water 20/80 to give 0.036 g (30%) of compound (64).

$^1$H NMR (500 MHz, DMSO-d$_6$) δ 8.81 (s, 1H), 8.33 (dd, J=1.1, 4.6 Hz, 1H), 8.17 (d, J=6.3 Hz, 2H), 8.02 (dd, J=1.1, 8.1 Hz, 1H), 7.37 (dd, J=4.6, 8.1 Hz, 1H), 7.13 (d, J=8.8 Hz, 4H), 6.80-6.87 (min 6H), 3.73 (s, 6H), 3.10-3.40 (m, 4H), 2.61-2.75 (m, 4H).

EXAMPLE 21

Preparation of compound (71)

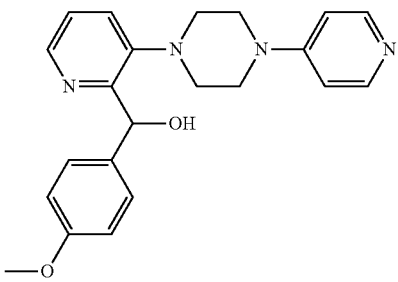

4-Methoxyphenylmagnesium bromide, 1M solution in THF (1.0 mL, 1.0 mmol) was added dropwise to a solution of intermediate (12) (0.26 g, 0.97 mmol) in THF (3 mL) at 0° C. The reaction mixture was stirred at 0° C. for 1 hour. The reaction mixture was poured into a solution of $NH_4Cl$ saturated, extracted with $CH_2Cl_2$. The organic layer was separated and evaporated till dryness to give 0.37 g of a crude product. It was crystallized from hot EtOH to give fraction 1 (0.14 g, 38%) and fraction 2 (0.04 g, 11%), 0.066 g of the fraction 1 were purified by flash chromatography over silica gel (30 m. Cartridge 12 g, from $CH_2Cl_2$ to $CH_2Cl_2/CH_3OH/NH_4OH$: 95/5/0.5) to yield 0.045 g of compound (71).

EXAMPLE 22

Preparation of compound (72)

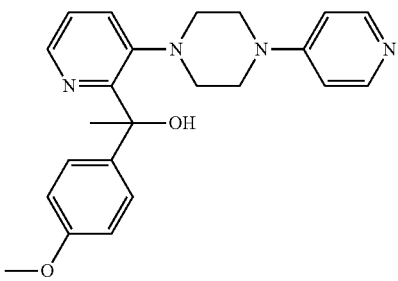

A mixture of compound (71) (0.1 g, 0.266 mmol) and $MnO_2$ (0.23 g, 2.66 mmol) in $CH_2Cl_2$ (2 mL) was stirred 2 days at room temperature. The mixture was filtered through a short pad of Celite® and the filtrate was evaporated till dryness (0.07 g). An additional amount of $MnO_2$ (0.12 g, 1.33 mmol) was added to a solution of the product in $CH_2Cl_2$ then stirred 18 hours at room temperature. The mixture was filtered through a short pad of Celite® and the filtrate was evaporated till dryness to give a crude product (0.07 g). Purification of the crude product was carried out by flash chromatography over silica gel (30 m. Cartridge 12 g, from $CH_2Cl_2$ to $CH_2Cl_2/CH_3OH/NH_4OH$: 95/5/0.5). The pure fractions were collected, evaporated to dryness to yield product A. Methylmagnesium bromide (0.18 mL, 0.54 mmol) was added dropwise to a solution of product A (0.167 g, 0.446 mmol) in THF (2 mL) at 0° C. The reaction mixture was stirred at 0° C. for 1 hour. The reaction mixture was poured into a solution of $NH_4Cl$ saturated, extracted with $CH_2Cl_2$. The organic layer was separated, dried over $MgSO_4$, filtered and evaporated to dryness. The residue was crystallized from EtOH to give compound (72) (0.07 g, 40%).

$^1$H NMR (500 MHz, DMSO-$d_6$) δ 8.50 (d, J=4.7 Hz, 1H), 8.16 (d, J=6.3 Hz, 2H), 7.94 (d, J=7.6 Hz, 1H), 7.60 (s, 1H), 7.40 (dd, J=4.7, 7.6 Hz, 1H), 7.26 (d, J=8.8 Hz, 2H), 6.78-6.89 (m, 4H), 3.70 (s, 3H), 3.21-3.39 (m, 4H), 2.58-2.68 (m, 4H), 1.78 (s, 3H).

EXAMPLE 23

Preparation of compound (76)

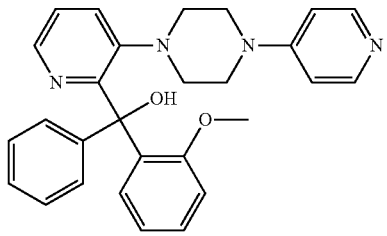

Under nitrogen flow a solution of KHMDS 0.7M in toluene (52 mL, 36.4 mmol) was added dropwise to a solution of intermediate (1) (4.0 g, 14.6 mmol) and benzyl cyanide (3.34 mL, 29.1 mmol) in DMF (40 mL) at room temperature, then the mixture was stirred for 10 min at room temperature and at 120° C. for 18 hours then an airflow was passed through the reaction mixture for 5 hours at 120° C. The reaction mixture was cooled to room temperature, poured out into water, extracted twice with EtOAc, the combined organic layer were washed with water then brine, dried ($MgSO_4$) and evaporated till dryness. The crude product was purified by flash chromatography over silica gel (30 µm, Cartridge 200 g. from $CH_2Cl_2$ to $CH_2Cl_2/CH_3OH/NH_4OH$: 93/7/0.7) The pure fractions were collected and evaporated to dryness yielding product B. 2-Methoxyphenylmagnesium bromide (0.70 mL, 0.70 mmol) was added dropwise to a solution of product B (0.2 g, 0.58 mmol) in DMF (2 mL) at −78° C., under nitrogen flow. The reaction mixture was stirred at −78° C. for 3 hours. A solution of $NH_4Cl$ 10% and $CH_2Cl_2$ were added, the organic layer was separated (hydrophobic frit) and evaporated till dryness. The crude product was purified by flash chromatography over silica gel (30 µm, Cartridge 12 g, from $CH_2Cl_2$ to $CH_2Cl_2$: $CH_2Cl_2/CH_3OH/NH_4OH$ 95/5/0.5). The pure fractions were collected and evaporated to dryness a product which was crystallized from DIPE to give compound (76) (129 mg, 49%).

$^1$H NMR (500 MHz. DMSO-$d_6$) δ 8.62 (s, 1H), 8.30 (dd, J=1.4, 4.6 Hz, 1H), 8.17 (d, J=5.0 Hz, 2H), 7.93 (dd, J=1.4, 8.0 Hz, 1H), 7.54 (d, J=7.2 Hz, 2H), 7.15-7.36 (m, 5H), 6.91 (d, J=8.0 Hz, 1H), 6.83 (d, J=5.0 Hz, 2H), 6.66-6.78 (m, 2H), 3.10-3.45 (m, 7H-partially obscured by solvent peak), 2.64-2.92 (m, 4H).

EXAMPLE 24

Preparation of compound (56)

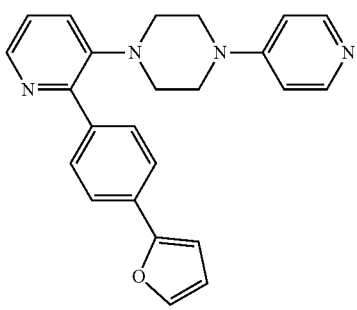

The reaction was performed under nitrogen atmosphere. A solution of intermediate (1) (0.80 g, 2.912 mmol) and 4-(fur-2-yl) benzeneboronic acid pinacol ester (1.81 g, 6.7 mmol) in potassium carbonate solution 2M (2.91 mL, 5.823 mmol) and DME (12 mL) was purged with nitrogen for 5 minutes then tetrakis (triphenylphosphine) palladium (0.336 g, 0.291 mmol) was added, the mixture was heated at 100° C. using a singlemode microwave (Biotage initiator 60) with a power output ranging from 0 to 400 W for 30 minutes. The mixture was poured out into water and $CH_2Cl_2$, the organic layer was separated, washed with water, dried over $MgSO_4$ and evaporated till dryness to give 2.50 g of a crude product. The crude product was purified by preparative LC on (Irregular SiOH 20-45 μm 450 g MATREX), mobile phase (40% heptane, 10% MeOH (+10% $NH_4OH$), 50% AcOEt). The good fractions are collected and the solvent was evaporated to give 0.78 g of the awaited compound, this was triturated from diethyl-ether, filtered and dried under vacuum at 60° C., yielding 0.72 g (64%) of compound (56).

$^1$H NMR (500 MHz, DMSO-$d_6$) δ 8.33 (d, J=4.5 Hz, 1H), 8.14 (d, J=6.3 Hz, 2H), 8.08 (d, J=8.51 Hz, 2H), 7.73-7.85 (m, 3H), 7.54 (d, J=7.6 Hz, 1H), 7.33 (dd, J=4.5, 7.6 Hz, 1H), 7.01 (d, J=3.2 Hz, 1H), 6.82 (d, J=6.3 Hz, 2H), 6.62 (dd, J=1.6, 3.2 Hz, 1H), 3.26-3.40 (m, 4H), 2.87-3.02 (m, 4H).

Compound (59) was prepared analogously starting from intermediate (1) and 4-biphenyl-boronic acid. Yield: 0.093 g (33%).

Compound (60) was prepared analogously starting from intermediate (1) and 4-(1-piperidinyl)benzene boronic acid pinacol ester. Yield: 0.180 g (69%).

Compound (61) was prepared analogously starting from intermediate (1) and 4-cyclohexyl-benzeneboronic acid. Yield: 0.130 g (50%).

Compound (62) was prepared analogously starting from intermediate (1) and 4-(4-methoxyphenyl)benzeneboronic acid. Yield: 0.169 g (61%).

Compound (63) was prepared analogously starting from intermediate (1) and 2-[3-(2-furanyl)phenyl]-4,4,5,5-tetramethyl 1,3,2-dioxaborolane. Yield: 0.016 g (6%).

Compound (65) was prepared analogously starting from intermediate (1) and intermediate (7). Yield: 0.081 g (28%).

$^1$H NMR (500 MHz, DMSO-$d_6$) δ 8.32 (d, =4.1 Hz, 1H), 8.15 (d, J=6.3 Hz, 2H), 8.06 (d, J=8.5 Hz, 2H), 7.72 (d, J=8.5 Hz, 2H), 7.53 (d, J=8.20 Hz, 1H), 7.32 (dd, J=4.1, 8.2 Hz, 1H), 6.87 (d, J=1.9 Hz, 1H), 6.83 (d, J=6.3 Hz, 2H), 6.22 (d, J=1.9 Hz, 1H), 3.24-3.41 (m, 4H), 3.0-2.89 (m, 4H), 2.35 (s, 3H).

Compound (66) was prepared analogously starting from intermediate (1) and intermediate (14). Yield: 0.024 g (12%).

$^1$H NMR (500 MHz, DMSO-$d_6$) δ 8.32 (dd, J=1.3, 4.4 Hz, 1H), 8.18 (s, 1H), 8.15 (d, J=6.3 Hz, 2H), 8.01 (d, J=8.5 Hz, 2H), 7.91 (s, 1H), 7.64 (d, J=8.5 Hz, 2H), 7.52 (dd, J=1.3, 8.2 Hz, 1H), 7.30 (dd, J=4.4, 8.20 Hz, 1H), 6.83 (d, J=6.3 Hz, 2H), 3.87 (s, 3H), 3.36-3.31 (m, 4H), 2.92-2.98 (m, 4H).

Compound (67) was prepared analogously starting from intermediate (1) and 1-methyl-5-[4-(4,4,5,5-tetramethyl-1,3,2-dioxaborolan-2-yl)phenyl]-1H-pyrazole. Yield: 0.013 g (10%).

EXAMPLE 26

Preparation of compound (69)

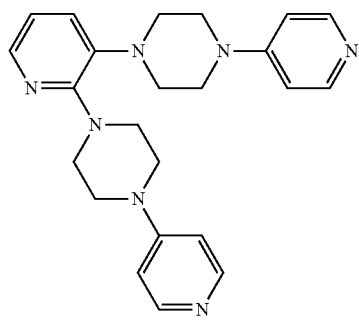

The reaction was made under nitrogen atmosphere. A mixture of intermediate (16) (250 mg, 0.783 mmol), 1-(4-pyridyl)piperazine (153.4 mg, 0.94 mmol), sodium tert-butoxide (105.37 mg, 1.096 mmol) in toluene (4 mL) was purged under nitrogen atmosphere, 9,9-Dimethyl-4,5-bis (diphenylphosphino)xanthenes (30.2 mg, 0.0522 mmol) then tris(dibenzylideneacetone)dipalladium(0) (17.9 mg, 0.0196 mmol) was added portionwise at room temperature in a sealed tube. The reaction mixture was heated at 110° C. for 18 hours. The reaction mixture was cooled down to room temperature. The mixture was poured out into water, extracted with EtOAc, the mixture was filtered through a short pad of Celite®, the organic layer was separated, washed with water and brine, dried over $MgSO_4$, evaporated till dryness and the residue was purified by preparative LC (stationary phase: irregular 15-40 μm 30 g Merck), mobile phase: 0.5% $NH_4OH$, 93% $CH_2Cl_2$, 7% MeOH). The pure fractions were collected and the solvent was evaporated to afford 0.115 g of the desired compound. The awaited product was crystallized from DIPE, filtered and dried under vacuum at 60° C. to afford 0.098 g (31%) of compound (69).

$^1$H NMR (500 MHz. DMSO-$d_6$) δ 8.12-8.25 (m, 4H), 7.93 (d, J=3.9 Hz, 1H), 7.29 (d, J=7.7 Hz, 1H), 6.96 (dd, J=3.9, 7.7 Hz, 1H), 6.83-6.93 (m, 4H), 3.42-3.57 (m, 12H), 3.24-3.12 (m, 4H).

EXAMPLE 27 a) Preparation of

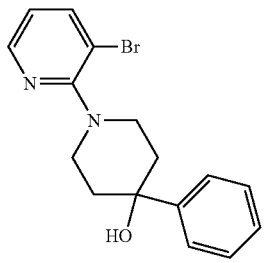

intermediate (17)

A solution of 3-bromo-2-chloropyridine (0.6 g, 3.12 mmol), 4-hydroxy-4-phenyl-piperidine (1.66 g, 9.35 mmol) and potassium carbonate (1.72 g, 12.47 mmol) in CH$_3$CN (8 mL) was stirred and heated at 80° C. for 18 hours. The solution was cooled down to room temperature. The mixture was poured out into water, extracted with EtOAc, the organic layer was separated, washed with water and brine, dried over MgSO$_4$ and evaporated till dryness. CH$_2$Cl$_2$ was added and the precipitate was filtered off, washed with DIPE and dried under vacuum at 60° C. affording 801 mg of intermediate (17) (insoluble) as a beige powder. Purification of filtrate was carried out by flash chromatography over silica gel (40 g, Heptane/EtOAc from 98/2 to 85/15). Pure fractions were collected and the solvent was evaporated to give intermediate (17) as a colorless oil (0.104 g, 10%).

Preparation of

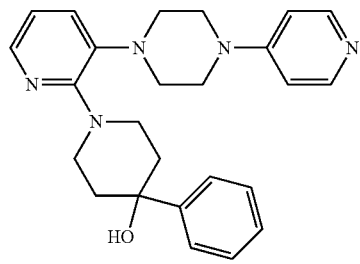

compound (73)

A mixture of intermediate (17) (0.104 g, 0.31 mmol), 1-(4-pyridyl)piperazine (0.061 g, 0.37 mmol), sodium tert-butoxide (0.042 g, 0.44 mmol), 9,9-dimethyl-4,5-bis(diphenyl-phosphino)xanthenes (0.009 g, 0.016 mmol) and tris(dibenzylidene-acetone)dipalladium (0) (0.007 g, 0.0078 mmol) in 1,4-dioxane (3 mL) was heated at 100° C. for 18 hours. The solution was cooled down to room temperature. The mixture was poured out into water, extracted with EtOAc, the mixture was filtered through a short pad of Celite®, the organic layer was separated, washed with water and brine, dried (MgSO$_4$) and evaporated till dryness. The crude product was purified by preparative LC (stationary phase: Spherical bare silica 5 μm 150×30.0 mm), mobile phase: gradient from 0.3% NH$_4$OH, 97%, CH$_2$Cl$_2$, 3% MeOH to 1.3% NH$_{40}$H, 87% CH$_2$Cl$_2$, 13% MeOH). Pure fractions were collected and the solvent was removed to give 0.01 g of the desired compound. It was freeze-dried with Acetonitrile/water 20/80 to give compound (73) as a white powder (0.010 g, 8%).

$^1$H NMR (500 MHz. DMSO-d$_6$) δ 8.18 (d, J=6.3 Hz, 2H), 7.90 (d, J=3.8 Hz, 1H), 7.52 (d, J=7.6 Hz, 2H), 7.34 (t, J=7.6 Hz, 2H), 7.23 (t, J=7.6 Hz, 2H), 6.87-6.92 (m, 3H), 4.98 (br. s., 1H), 4.03 (d, J=12.0 Hz, 2H), 3.46-3.53 (m, 4H), 3.15-3.22 (m, 4H), 3.11 (t, J=12.0 Hz, 2H), 2.04 (dt, J=4.1, 12.0 Hz, 2H), 1.75 (d, J=12.0 Hz, 2H).

EXAMPLE 28

Preparation of

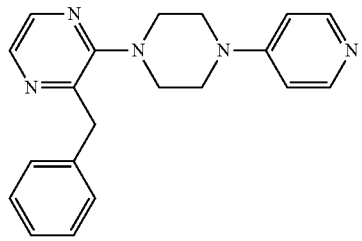

compound (53)

Nitrogen was bubbled for 5 minutes through a solution intermediate (18) (350 mg, 1.27 mmol), benzylzinc bromide solution 0.5 M in tetrahydrofuran (7.6 mL, 3.8 mmol) in THF (10 mL). Dichloro[1,1'-bis (diphenylphosphino) ferrocene] palladium (II) dichloromethane adduct (210 mg, 0.254 mmol) was added and the cap was sealed and the mixture was stirred at 70° C. for 16 hours. The reaction was cooled down to room temperature. Water was added and the product was extracted with ethyl acetate: the organic layer was washed with water, brine dried over MgSO$_4$, filtered and the solvent was evaporated to afford 200 mg of a crude product. It was purified by preparative LC on (Stability Silica 5 μm 150×30.0 mm), mobile phase (gradient from 0% NH$_4$OH, 100% CH$_2$Cl$_2$, 0% MeOH to 0.8% NH$_4$OH, 92% CH$_2$Cl$_2$, 8% MeOH). The pure fractions were collected and the solvent was evaporated to afford compound (53) (0.048 g, 11%).

$^1$H NMR (500 MHz, DMSO-d$_6$) δ 8.13-8.25 (m, 4H), 7.16-7.33 (m, 5H), 6.87 (d, J=6.6 Hz, 2H), 4.21 (s, 2H), 3.42-3.50 (m, 4H), 3.18-3.25 (m, 4H).

EXAMPLE 29

Preparation of

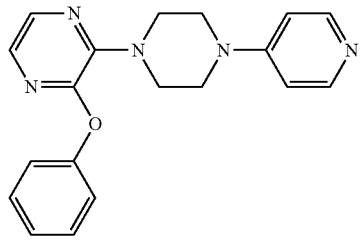

compound (54)

A mixture of intermediate (18) (1 g, 3.627 mmol), phenol (0.512 g, 5.44 mmol), K$_2$CO$_3$ (1 g, 7.253 mmol) in DMF (15 mL) was stirred at 80° C. 18 hours. The reaction mixture was cooled down to room temperature, the mixture was poured into ice water and ethyl acetate was added. The organic layer was separated, dried under MgSO$_4$, filtered and dried under vacuum to afford 1.2 g of a crude product. It was purified by achiral SFC on (cyano 6 μm 150×21.2 mm), mobile phase (0.3% isopropylamine, 80% CO$_2$, 20% MeOH) to afford 0.160 g of the desired compound. This compound was triturated from diethylether, filtered and dried under vacuum at 60° C., yielding 0.148 g (12%) of compound (54).

$^1$H NMR (500 MHz, DMSO-d$_6$) δ 8.18 (d, J=6.3 Hz, 2H), 7.94 (d, J=2.8 Hz, 1H), 7.57 (d, J=2.8 Hz, 1H), 7.44 (t, J=7.9 Hz, 2H), 7.25 (t, J=7.9 Hz, 1H), 7.20 (d, J=7.9 Hz, 2H), 6.87 (d, J=6.3 Hz, 2H), 3.65-3.73 (m, 4H), 3.45-3.53 (m, 4H).

EXAMPLE 30

Preparation of compound (55)

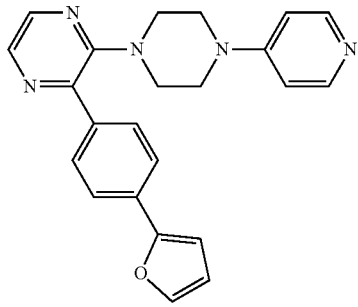

To a solution of intermediate (18) (170 mg, 0.62 mmol) in DME (3 mL) was added 2-(4-(2-furanyl)phenyl)-4,4,5,5-tetramethyl-1,3,2-dioxaborolane (174 mg, 0.64 mmol) and potassium carbonate solution 2M (0.7 mL, 1.3 mmol) the reaction mixture was degazed with nitrogen for 15 minutes then tetrakis(triphenylphosphine)palladium(0) (7 mg, 0.006 mmol) was added and the mixture was heated at 100° C. using a single mode microwave (Biotage Initiator EXP 60) with a power output ranging from 0 to 400 W for 40 minutes. Water was added and the product was extracted with ethyl acetate, the organic layer was washed twice with water, then brine, dried over MgSO$_4$, filtered and the solvent was evaporated to afford 220 mg of a crude product.

The crude product was purified by preparative LC on (Stability Silica 5 μm 150×30.0 mm), mobile phase (gradient from 0.2% NH$_4$OH, 2% MeOH, 98% CH$_2$Cl$_2$ to 0.8% NH$_4$OH, 8% MeOH, 92% CH$_2$Cl$_2$). The pure fractions were collected, the solvent was evaporated and the resulting product was crystallized from diethyl ether, filtered and dried to give (0.026 g, 11%) of compound (55).

$^1$H NMR (500 MHz. DMSO-d$_6$) δ 8.25 (d, J=2.5 Hz, 1H), 8.21 (d, J=2.5 Hz, 1H), 8.15 (d, J=6.3 Hz, 2H), 8.02 (d, J=8.5 Hz, 2H), 7.83 (d, J=8.5 Hz, 2H), 7.80 (d, J=1.1 Hz, 1H), 7.05 (d, J=3.2 Hz, 1H), 6.82 (d, J=6.3 Hz, 2H), 6.64 (dd, J=1.1, 3.2 Hz, 1H), 3.35-3.41 (m, 4H), 3.22-3.28 (m, 4H).

Table A-1 lists the compounds that were prepared according to one of the above Examples.

TABLE A-1

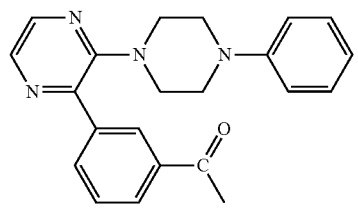

Co. No. 1; Ex. 1

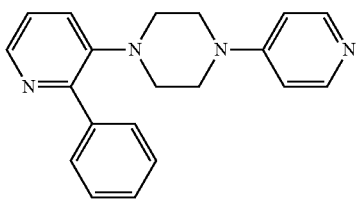

Co. No. 2; Ex. 4

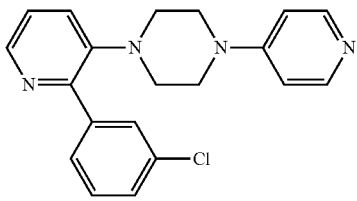

Co. No. 3; Ex. 4

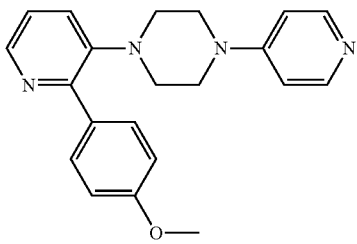

Co. No. 4; Ex. 4

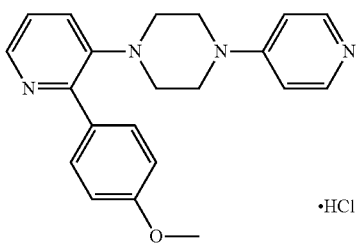

Co. No. 5; Ex. 4

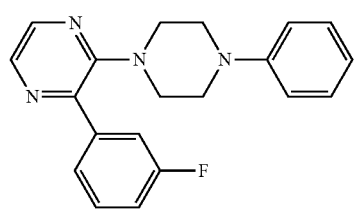

Co. No. 6; Ex. 2

TABLE A-1-continued
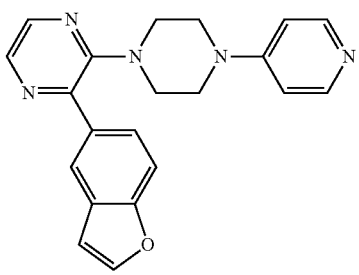
Co. No. 7; Ex. 2
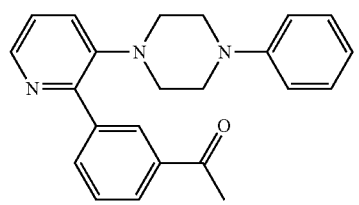
Co. No. 8; Ex. 4
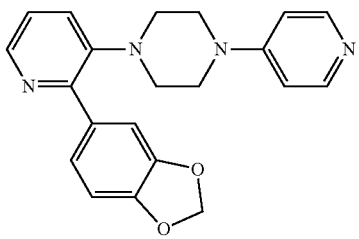
Co. No. 9; Ex. 4
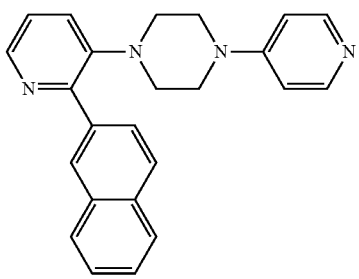
Co. No. 10; Ex. 5
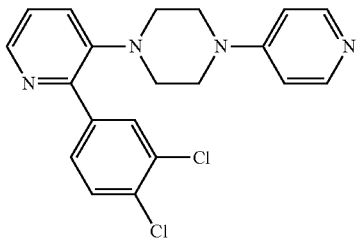
Co. No. 11; Ex. 4
TABLE A-1-continued
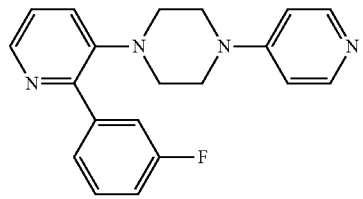
Co. No. 12; Ex. 4
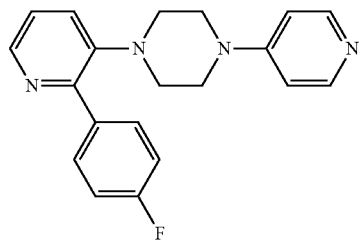
Co. No. 13; Ex. 4
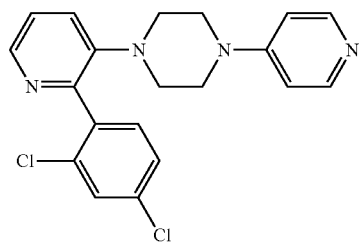
Co. No. 14; Ex. 4
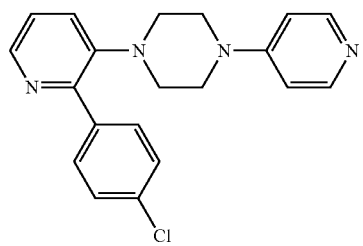
Co. No. 15; Ex. 4
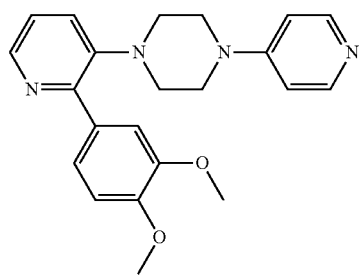
Co. No. 16; Ex. 4

TABLE A-1-continued
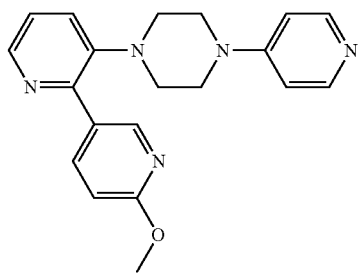
Co. No. 17; Ex. 4
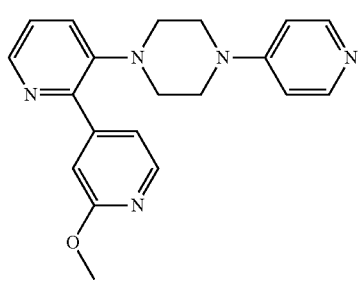
Co. No. 18; Ex. 4
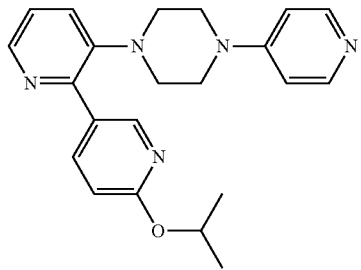
Co. No. 19; Ex. 4
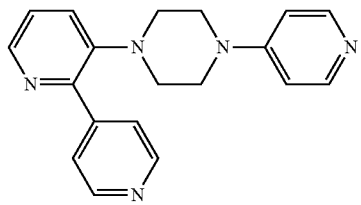
Co. No. 20; Ex. 4
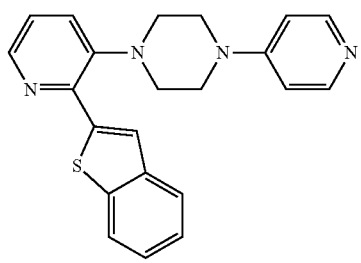
Co. No. 21; Ex. 4
TABLE A-1-continued
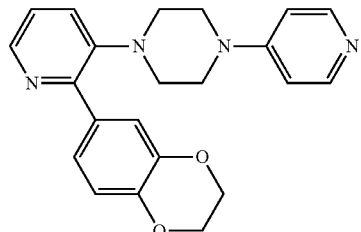
Co. No. 22; Ex. 4
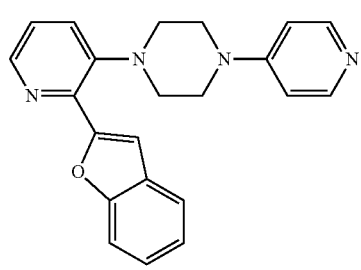
Co. No. 23; Ex. 5
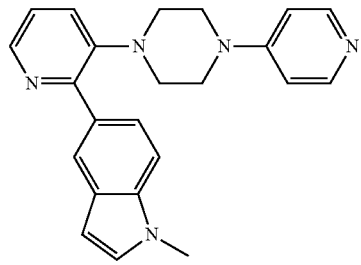
Co. No. 24; Ex. 5
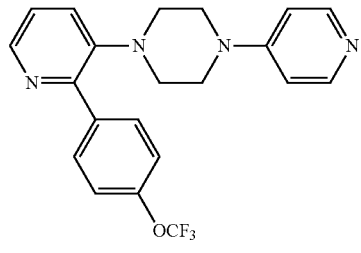
Co. No. 25; Ex. 4
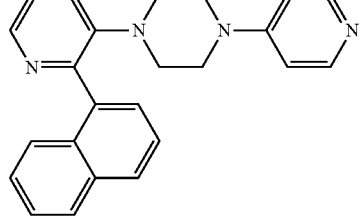
Co. No. 26; Ex. 5

TABLE A-1-continued

Co. No. 27; Ex. 4

Co. No. 28; Ex. 4

Co. No. 29; Ex. 14

Co. No. 30; Ex. 4

Co. No. 31; Ex. 4

Co. No. 32; Ex. 14

Co. No. 33; Ex. 4

Co. No. 34; Ex. 4

Co. No. 35; Ex. 4

Co. No. 36; Ex. 3

TABLE A-1-continued
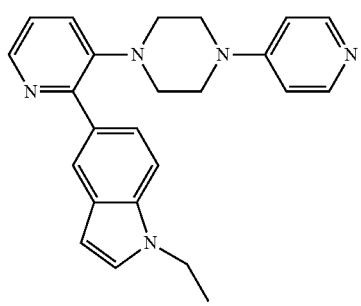
Co. No. 37; Ex. 16
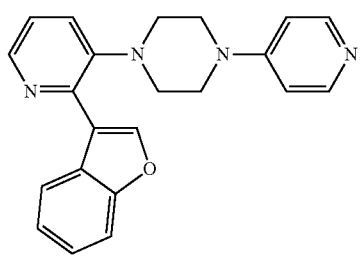
Co. No. 38; Ex. 4
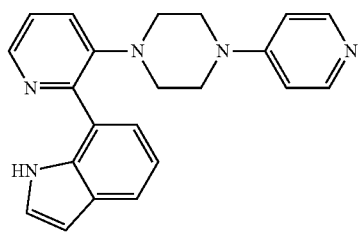
Co. No. 39; Ex. 4
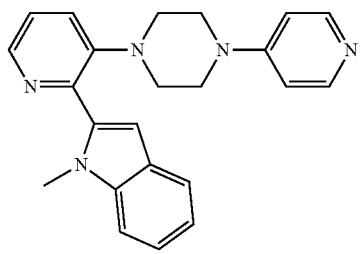
Co. No. 40; Ex. 4
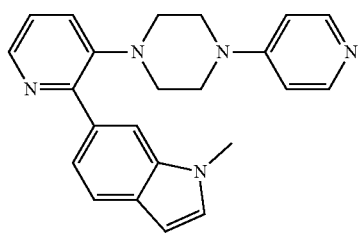
Co. No. 41; Ex. 5
TABLE A-1-continued
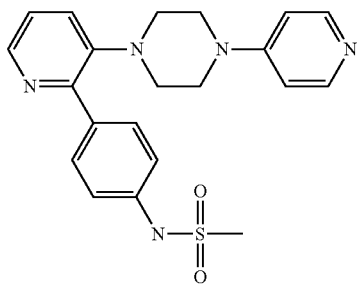
Co. No. 42; Ex. 4
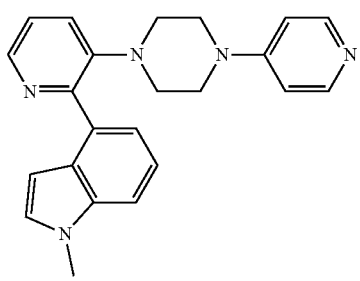
Co. No. 43; Ex. 15
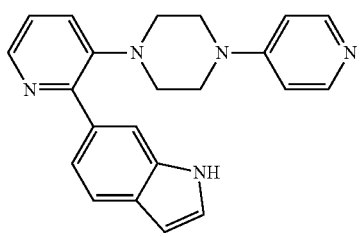
Co. No. 44; Ex. 6
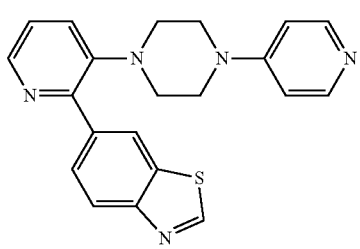
Co. No. 45; Ex. 4
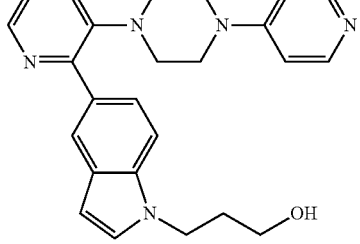
Co. No. 46; Ex. 17

TABLE A-1-continued
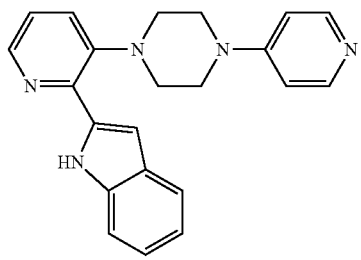
Co. No. 47; Ex. 11
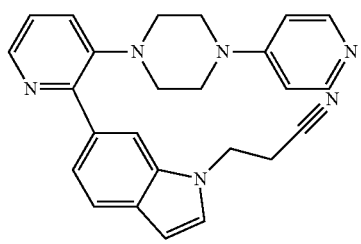
Co. No. 48; Ex. 8
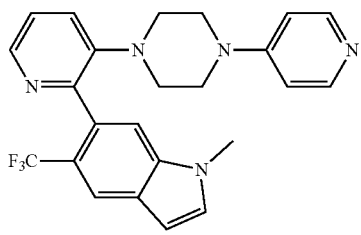
Co. No. 49; Ex. 10
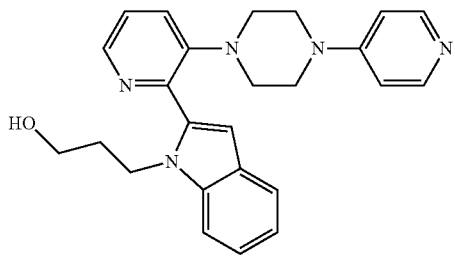
Co. No. 50; Ex. 12
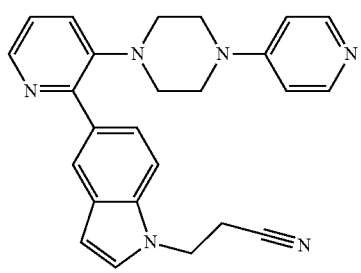
Co. No. 51; Ex. 9
TABLE A-1-continued
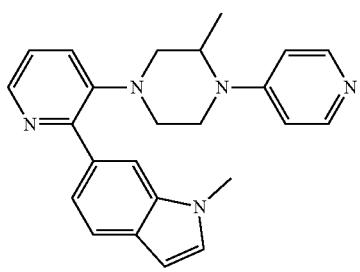
Co. No. 52; Ex. 18
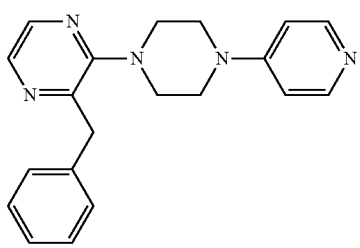
Co. No. 53; Ex. 28
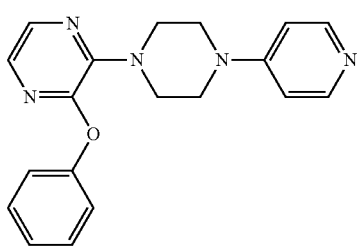
Co. No. 54; Ex. 29
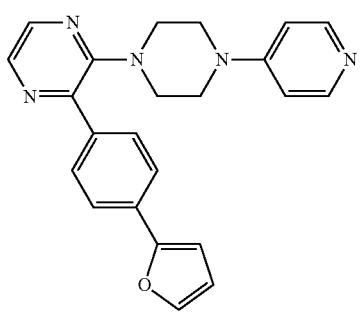
Co. No. 55; Ex. 30
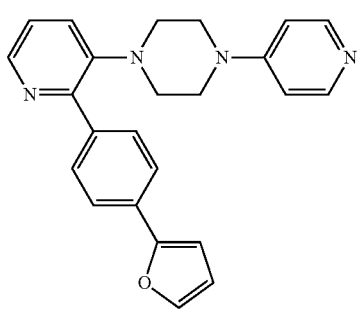
Co. No. 56; Ex. 24

TABLE A-1-continued
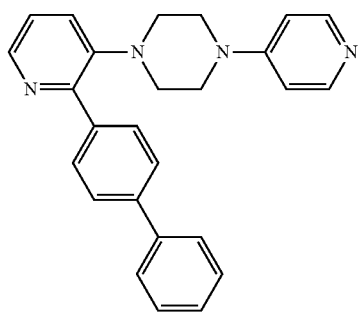
Co. No. 59; Ex. 24
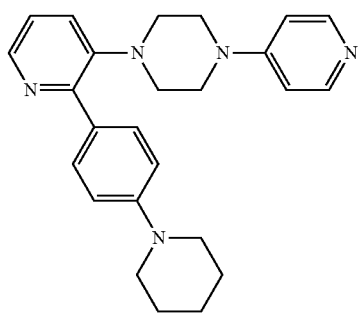
Co. No. 60; Ex. 24
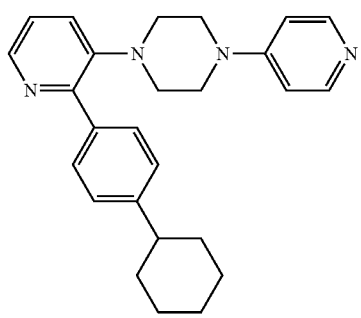
Co. No. 61; Ex. 24
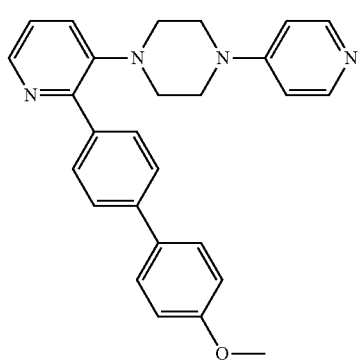
Co. No. 62; Ex. 24
TABLE A-1-continued
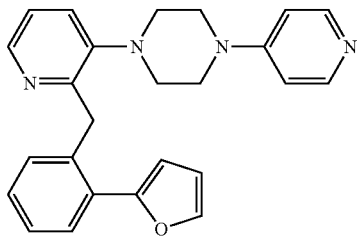
Co. No. 63; Ex. 24
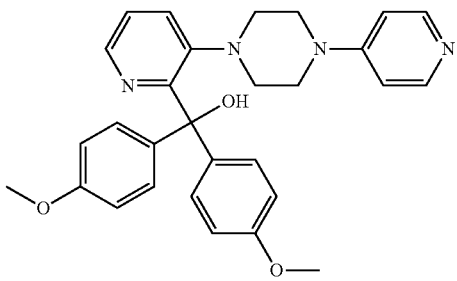
Co. No. 64; Ex. 20
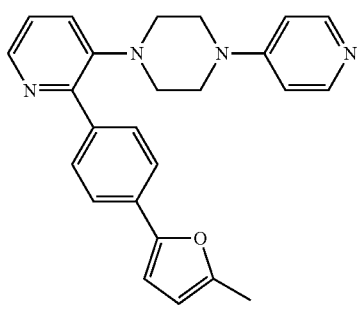
Co. No. 65; Ex. 25
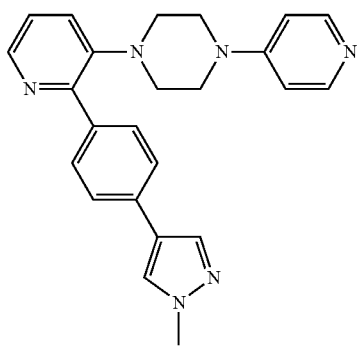
Co. No. 66; Ex. 24

TABLE A-1-continued
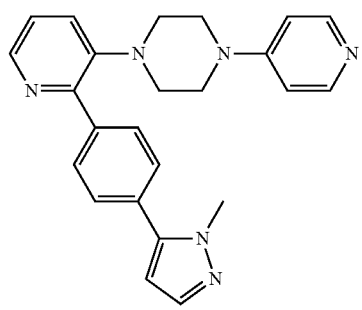
Co. No. 67; Ex. 24
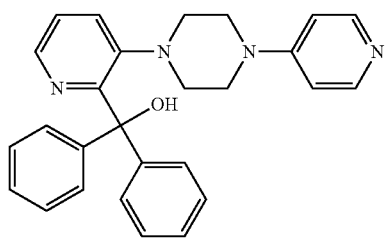
Co. No. 68; Ex. 19
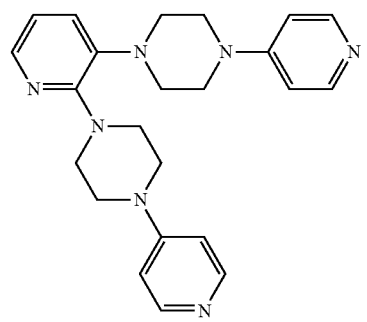
Co. No. 69; Ex. 26
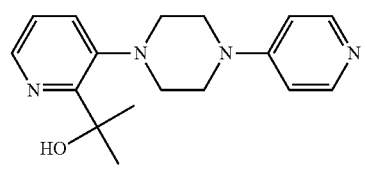
Co. No. 70; Ex. 19
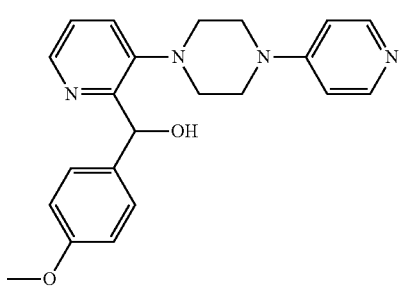
Co. No. 71; Ex. 21
TABLE A-1-continued
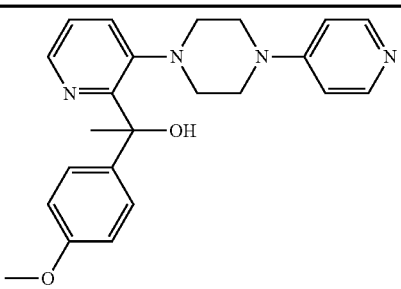
Co. No. 72; Ex. 22
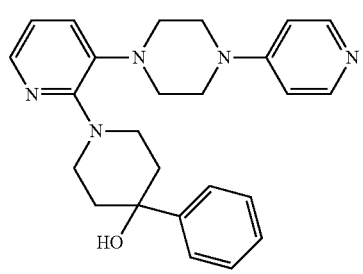
Co. No. 73; Ex. 27
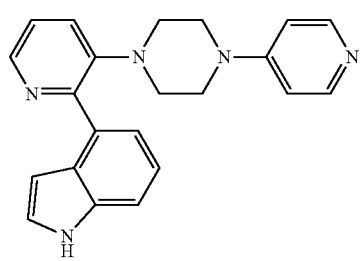
Co. No. 74; Ex. 7
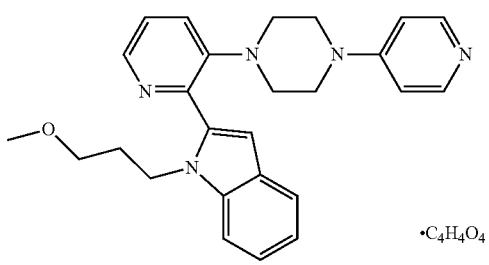
•$C_4H_4O_4$
Co. No. 75; Ex. 13
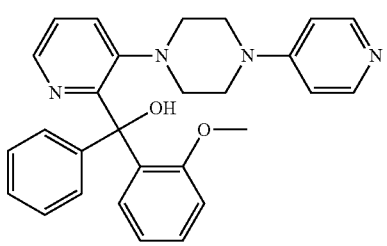
Co. No. 76; Ex. 23
•$C_4H_4O_4$: fumarate salt

B. Analytical Part

B.1. LC-MS General Procedure 1

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (R) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE B-1

LCMS Method codes (Flow expressed in mL/min; column temperature (T) in ° C.; Run time in minutes).

| Instrument | Column | Mobile phase | gradient | Flow Column T | Run time |
|---|---|---|---|---|---|
| Waters: Acquity UPLC ®-DAD and Quattro Micro ™ | Waters: BEH C18 (1.7 µm, 2.1 × 100 mm) | A: 9.5% $CH_3COONH_4$ 7 mM/5% $CH_3CN$, B: $CH_3CN$ | 84.2% A for 0.49 min, to 10.5% A in 2.18 min, held for 1.94 min, back to 84.2% AB in 0.73 min, held for 0.73 min. | 0.343 40 | 6.2 |
| Waters: Acquity UPLC ® H-Class-DAD and SQD 2 | Waters: BEH C18 (1.7 µm, 2.1 × 100 mm) | A: 95% $CH_3COONH_4$ 7 mM/5% $CH_3CN$, B: $CH_3CN$ | 84.2% A for 0.49 min, to 10.5% A in 1.81 min, held for 2.31 min, back to 84.2% A in 0.73 min, held for 0.73 min. | 0.343 40 | 6.1 |

B.2. Melting Points

For a number of compounds, melting points (m.p.) were determined with DSC apparatus using a temperature gradient of 10° C./minute.

For a number of compounds, melting points were obtained with a Kofler hot bench, consisting of a heated plate with linear temperature gradient, a sliding pointer and a temperature scale in degrees Celsius.

TABLE B-2

LC/MS data and melting points

| Co. No. | Rt | LC-MS (MH+) | procedure | mp. (° C.) (DSC) | MP. (° C.) Kofler |
|---|---|---|---|---|---|
| 1 | 3.32 | 359 | 1 | 172.56° C. (25° C. to 250° C./10° C. min) | — |
| 2 | 2.25 | 317 | 1 | 204.15° C. (25° C. to 250° C./10° C. min) | 203° C. |
| 3 | 2.58 | 351 | 1 | — | — |
| 4 | 2.26 | 347 | 1 | — | 216° C. |
| 5 | 2.26 | 347 | 1 | — | — |
| 6 | 3.61 | 335 | 1 | 139.51° C. (25° C. to 200° C./10° C. min) | 186° C. |
| 7 | 2.42 | 358 | 1 | — | — |
| 8 | 3.26 | 358 | 1 | 175.94° C. (25° C. to 220° C./10° C. min) | 176° C. |
| 9 | 2.22 | 361 | 1 | 187.80° C. (25° C. to 250° C./10° C. min) | 188° C. |
| 10 | 2.64 | 367 | 1 | 162.05° C. (25° C. to 250° C./10° C. min) | 162° C. |
| 11 | 2.86 | 385 | 1 | 159.50° C. (25° C. to 250° C./10° C. min) | 159° C. |
| 12 | 2.35 | 335 | 1 | 184.88° C. (25° C. to 220° C./10° C. min) | 184° C. |
| 13 | 2.33 | 335 | 1 | 173.62° C. (25° C. to 220° C./10° C. min) | — |
| 14 | 2.59 | 385 | 1 | — | — |
| 15 | 2.56 | 351 | 1 | — | — |
| 16 | 2.09 | 377 | 1 | — | — |
| 17 | 2.01 | 348 | 1 | — | 138° C. |
| 18 | 1.98 | 348 | 1 | — | — |

TABLE B-2-continued

LC/MS data and melting points

| Co. No. | Rt | LC-MS (MH+) | procedure | mp. (° C.) (DSC) | MP. (° C.) Kofler |
|---|---|---|---|---|---|
| 19 | 2.43 | 376 | 1 | — | — |
| 20 | 1.64 | 318 | 1 | — | 166° C. |
| 21 | 2.89 | 373 | 1 | — | 224° C. |
| 22 | 2.21 | 375 | 1 | — | 88° C. |
| 23 | 2.43 | 357 | 1 | — | 252° C. |
| 24 | 2.38 | 370 | 1 | — | 197° C. |
| 25 | 2.76 | 401 | 1 | — | 176° C. |
| 26 | 2.44 | 367 | 1 | — | 90° C. |
| 27 | 2.36 | 357 | 1 | — | 192° C. |
| 28 | 2.77 | 342 | 2 | — | — |
| 29 | 3.58 | 347 | 2 | — | — |
| 30 | 2.81 | 359 | 2 | — | 200° C. |
| 31 | 1.83 | 368 | 1 | — | 96° C. |
| 32 | 2.94 | 351 | 1 | — | 122° C. |
| 33 | 2.13 | 368 | 1 | — | 182° C. |
| 35 | 2.48 | 363 | 1 | — | 160° C. |
| 36 | 2.11 | 356 | 1 | — | 252° C. |
| 37 | 2.47 | 384 | 1 | — | 110° C. |
| 38 | 2.63 | 357 | 1 | — | 210° C. |
| 39 | 2.28 | 356 | 1 | — | 162° C. |
| 40 | 2.46 | 370 | 1 | — | — |
| 41 | 2.34 | 370 | 1 | 174.57° C. (25° C. to 300° C./10° C. min) | — |
| 42 | 1.9 | 410 | 1 | — | 248° C. |
| 43 | 2.22 | 370 | 1 | — | 170° C. |
| 44 | 2.15 | 356 | 1 | — | 195° C. |
| 45 | 2.03 | 374 | 1 | — | 196° C. |
| 46 | 2.05 | 414 | 1 | — | 110° C. |
| 49 | 2.52 | 438 | 1 | — | 120° C. |
| 50 | 2.21 | 414 | 1 | — | 110° C. |
| 52 | 2.46 | 384 | 1 | — | — |
| 53 | 2.4 | 332 | 1 | — | — |
| 54 | 2.46 | 334 | 1 | — | 130° C. |
| 55 | 2.75 | 384 | 1 | 153.75° C. (25° C. to 200° C./10° C. min) | — |
| 56 | 2.66 | 383 | 1 | 224.32° C. (25° C. to 350° C./10° C. min) | 224° C. |
| 59 | 2.87 | 393 | 1 | — | 98° C. |
| 60 | 2.79 | 400 | 1 | — | 92° C. |
| 61 | 3.35 | 399 | 1 | — | — |
| 62 | 2.77 | 423 | 1 | — | 178° C. |
| 63 | 2.6 | 383 | 1 | — | — |
| 64 | 2.59 | 483 | 1 | — | — |
| 65 | 2.82 | 397 | 1 | — | 230° C. |
| 66 | 2.09 | 397 | 1 | — | — |
| 67 | 2.15 | 397 | 1 | — | — |
| 68 | 2.67 | 423 | 1 | — | 260° C. |
| 69 | 1.81 | 402 | 1 | — | 186° C. |
| 70 | 1.59 | 299 | 1 | — | 163° C. |
| 71 | 2.09 | 377 | 1 | — | — |
| 72 | 2.28 | 391 | 1 | — | — |
| 73 | 2.36 | 416 | 1 | — | — |
| 74 | 2.01 | 356 | 1 | — | 262° C. |
| 75 | 2.59 | 428 | 1 | — | 168° C. |
| 76 | 2.57 | 453 | 1 | — | — |

C. Pharmacological Examples

C.1 Antiviral Activity

Black 384-well clear-bottom microtiter plates (Corning, Amsterdam, The Netherlands) were filled via acoustic drop ejection using the echo liquid handler (Labcyte, Sunnyvale, Calif.), 200 nL of compound stock solutions (100% DMSO) were transferred to the assay plates, 9 serial 4-fold dilutions of compound were made, creating per quadrant the same compound concentration. The assay was initiated by adding 10 µL of culture medium to each well (RPMI medium without phenol red, 10% FBS-heat inactivated, 0.04% gentamycin (50 mg/mL). All addition steps are done by using a multidrop dispenser (Thermo Scientific, Erembodegem, Belgium). Next, rgRSV224 virus (MOI=1) diluted in culture medium was added to the plates, rgRSV224 virus is an engineered virus that includes an additional GFP gene (Hallak L K, Spillmann D. Collins P L, Peeples M E. Glycosaminoglycan sulfation requirements for respiratory syncytial virus infection; Journal of virology (2000), 74(22), 10508-13) and was in-licensed from the NIH (Bethesda, Md., USA). Finally, 20 µL of a HeLa cell suspension (3,000 cells/well) were plated. Medium, virus- and mock-infected controls were included in each test. The wells contain 0.05% DMSO per volume. Cells were incubated at 37° C. in a 5% CO2 atmosphere. Three days post-virus exposure, viral replication was quantified by measuring GFP expression in the cells by an in house developed MSM laser microscope (Tibotec. Beerse, Belgium). The EC50 was defined as the 50% inhibitory concentration for GFP expression. In parallel, compounds were incubated for three days in a set of white 384-well microtiter plates (Corning) and the cytotoxicity of compounds in HeLa cells was determined by measuring the ATP content of the cells using the ATPlite kit (PerkinElmer, Zaventem, Belgium) according to the manufacturer's instructions. The $CC_{50}$ was defined as the 50% concentration for cytotoxicity.

TABLE C-1 antiviral data

| Co. No. | RSV HELA pEC50 | TOX HELA pCC50 |
|---|---|---|
| 1 | 6.02 | 5.64 |
| 2 | 6.22 | 5.95 |
| 3 | 6.26 | <4 |
| 4 | 6.38 | <4.01 |
| 5 | 6.37 | <4 |
| 6 | 6.24 | <4 |
| 7 | 6.06 | <4.01 |
| 8 | 6.19 | <4 |
| 9 | 6.16 | <4 |
| 10 | 7.1 | 4.4 |
| 11 | 6.57 | 4.55 |
| 12 | 6.06 | <4 |
| 13 | 6.22 | <4.05 |
| 14 | 6.73 | 4.39 |
| 15 | 6.51 | 6.05 |
| 16 | 6.01 | <4 |
| 17 | 6.36 | <4.01 |
| 18 | 6.08 | <4.01 |
| 19 | 6.28 | 4.72 |
| 20 | 6.06 | <4 |
| 21 | 6.69 | 4.98 |
| 22 | 6.27 | 6.4 |
| 23 | 7.23 | <4.3 |
| 24 | 7.14 | 4.33 |
| 25 | 6.06 | 4.48 |
| 26 | 7.07 | 5.13 |
| 27 | 6.87 | 4.13 |
| 28 | 6.23 | <4 |
| 29 | 6.91 | 6.59 |
| 30 | 6.22 | 5.77 |
| 31 | 6.14 | <4.01 |
| 32 | 6.98 | 6.87 |
| 33 | 6.66 | <4 |
| 34 | 6.53 | 4.13 |
| 35 | 6.93 | 4.34 |
| 36 | 7.1 | 4.35 |
| 37 | 7.51 | 4.66 |
| 38 | 6.88 | 4.35 |
| 39 | 6.07 | 4.26 |
| 40 | 7.6 | 4.27 |
| 41 | 7.94 | 4.31 |
| 42 | 6.3 | <4 |
| 43 | 7.52 | 4.34 |
| 44 | 7.49 | 4.27 |
| 45 | 6.81 | <4 |
| 46 | 6.83 | 4.28 |
| 48 | 6.78 | <4 |
| 49 | 7.17 | 4.12 |
| 50 | 8.18 | <4 |
| 51 | 7.13 | 4.26 |
| 52 | 7.87 | 4.35 |
| 53 | 5.47 | 4.12 |
| 54 | 4.97 | 4.06 |
| 55 | 6.1 | 4.44 |
| 56 | 7.02 | 4.71 |
| 59 | 6.28 | 4.97 |
| 60 | 6.45 | 4.64 |
| 61 | 6.08 | 5.46 |
| 62 | 6.59 | 4.94 |
| 63 | 6.79 | 4.25 |
| 64 | 7.3 | <4.03 |
| 65 | 6.72 | 4.96 |
| 66 | 6.03 | 4.15 |
| 67 | 6.39 | 4.01 |
| 68 | 7.6 | <4.6 |
| 69 | 6.03 | 4.39 |
| 70 | 4.72 | <4 |
| 71 | 4.40 | <4 |
| 72 | 6.28 | <4 |
| 73 | 6.20 | 4.2 |

D. Prophetic Composition Examples

"Active ingredient" as used throughout these examples relates to a final compound of Formula (I), the pharmaceutically acceptable salts thereof, the solvates and the stereochemically isomeric forms and the tautomers thereof.

Typical examples of recipes for the formulation of the invention are as follows:

D.1. Tablets

| Active ingredient | 5 to 50 mg |
|---|---|
| Di calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

D.2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

D.3. Injectable

A parenteral composition is prepared by stirring 1.5% by weight of active ingredient of the invention in 10% by volume propylene glycol in water.

D.4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of the following formula

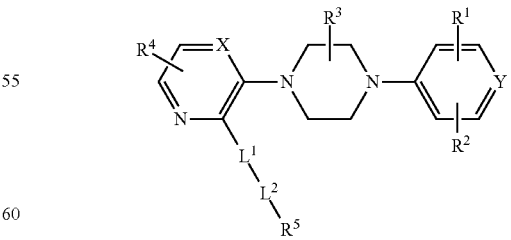

or a stereochemically isomeric form thereof, wherein
X is $CR^6$, and Y is N, wherein $R^6$ is hydrogen;
$R^1$ and $R^2$ are hydrogen;
$R^3$ is hydrogen;
$R^4$ is hydrogen;

L¹ is a direct bond;
L² is a direct bond; and
R⁵ is heteroaryl;
  wherein each heteroaryl is optionally substituted with one or two substituents each independently selected from the group consisting of: $C_{1-4}$alkyl, $C_{1-4}$alkyloxy, hydroxy$C_{1-4}$alkyl, cyano$C_{1-4}$alkyl, polyhalo$C_{1-4}$alkyl, and $C_{1-4}$alkyloxy$C_{1-4}$alkyl;
or a pharmaceutically acceptable acid addition salt thereof.

2. The compound as claimed in claim 1 wherein R⁵ is selected from the group consisting of: furanyl, thiophenyl, pyrazolyl, pyridinyl, pyridazinyl, pyrimidinyl, pyrazinyl, 2,3-dihydro-benzo[1,4]dioxinyl, benzo[1,3]dioxolyl, 1-benzofuranyl, 2,3-dihydro-1-benzofuranyl, 1-benzothiophenyl, benzopyrrolyl, 1-benzopyrazolyl, 1,3-benzothiazolyl, and quinolinyl.

3. The compound as claimed in claim 1 wherein the heteroaryl is pyridinyl optionally substituted with one or two substituents.

4. The compound as claimed in claim 1 wherein the heteroaryl is quinolinyl optionally substituted with one or two substitutents.

5. The compound as claimed in claim 1 wherein the heteroaryl is benzopyrrolyl optionally substituted with one or two substituents.

6. The compound as claimed in claim 1 wherein the heteroaryl is benzofuranyl optionally substituted with one or two substitutents.

7. The compound as claimed in claim 1 wherein the heteroaryl is benzothiazolyl optionally substituted with one or two substitutents.

8. A pharmaceutical composition comprising a pharmaceutically acceptable carrier and a therapeutically active amount of a compound as claimed in claim 1.

9. A process for preparing a pharmaceutical composition as claimed in claim 8 comprising intimately mixing the therapeutically active amount of a compound with a pharmaceutically acceptable carrier.

10. A method of treating a respiratory syncytial virus infection comprising administering a therapeutically effective amount of at least one compound of claim 1.

* * * * *